United States Patent
Newkome et al.

(10) Patent No.: US 10,208,069 B2
(45) Date of Patent: Feb. 19, 2019

(54) PRECISE THREE-DIMENSIONAL SUPRAMACROMOLECULE INTERCONVERSIONS

(71) Applicants: George R. Newkome, Medina, OH (US); Charles N. Moorefield, Chagrin Falls, OH (US); Tingzheng Xie, Akron, OH (US); Xiaocun Lu, Akron, OH (US)

(72) Inventors: George R. Newkome, Medina, OH (US); Charles N. Moorefield, Chagrin Falls, OH (US); Tingzheng Xie, Akron, OH (US); Xiaocun Lu, Akron, OH (US)

(73) Assignee: The University of Akron, Akron, OH (US)

( * ) Notice: Subject to any disclaimer, the term of this patent is extended or adjusted under 35 U.S.C. 154(b) by 174 days.

(21) Appl. No.: 15/013,220

(22) Filed: Feb. 2, 2016

(65) Prior Publication Data

US 2016/0222035 A1    Aug. 4, 2016

Related U.S. Application Data

(60) Provisional application No. 62/164,641, filed on May 21, 2015, provisional application No. 62/110,662, filed on Feb. 2, 2015.

(51) Int. Cl.
*C07F 3/06* (2006.01)
*C07D 213/22* (2006.01)

(52) U.S. Cl.
CPC ............. *C07F 3/06* (2013.01); *C07D 213/22* (2013.01)

(58) Field of Classification Search
CPC ........................... C07D 213/22; C07D 213/68
See application file for complete search history.

(56) References Cited

U.S. PATENT DOCUMENTS

| | | | |
|---|---|---|---|
| 3,678,072 A | 7/1972 | Faber et al. | |
| 5,863,919 A | 1/1999 | Newkome et al. | |
| 6,399,717 B1 | 6/2002 | Newkome et al. | |
| 7,250,534 B1 | 7/2007 | Newkome et al. | |
| 7,368,512 B2 | 5/2008 | Newkome et al. | |
| 7,811,675 B2 * | 10/2010 | Che | C07D 213/22 252/301.16 |
| 8,138,301 B2 | 3/2012 | Newkome et al. | |
| 9,059,409 B2 | 6/2015 | Newkome et al. | |
| 2009/0171088 A1 * | 7/2009 | Newkome | C08G 73/0627 546/10 |

OTHER PUBLICATIONS

Schubert (Synthetic metals; 121, 2001, 1249-1252).*
Graziano Vernizzi, "Faceting Ionic Shells into Icosahedra via Electrostatics," Proceedings of the National Academy of Sciences, Nov. 20, 2007, vol. 104, No. 47, 18382-18386.
Harvey T. McMahon, "Molecular Mechanism and Physiological Functions of Clathrin-Mediated Endocytosis," Nature Reviews/Molecular Cell Biology, Aug. 2011, vol. 12, 517-533.
Scott M. Stagg, "Structure of the Sec13,31 COPII Coat Cage," 2006 Nature Publishing Group, Jan. 2006, vol. 439, 234-238.
James E. Rothman, "The Nobel Prize in Physiology or Medicine 2013," Nobel Media AB 2014, Web. Mar. 3, 2015.
E.W. Weisstein, "Archimedian Solid," MathWorld Notebook—A Wolfram Web Resource, http://mathworld.wolfram.com/ArchimedianSolid.html.
Bogdan Olenyuk, "Self-Assembly of Nanoscale Cuboctahedra by Coordination Chemistry," Nature, Apr. 29, 1999, Macmillan Magazines Ltd., vol. 398, 796-799.
Leonard R. MacGillivray, "A Chiral Spherical Molecular Assembly Held Together by 60 Hydrogen Bonds," Nature, Oct. 2, 1997, Macmillan Publishers Ltd., vol. 398, 469-472.
Yuzhou Liu, "Supramolecular Archimedean Cages Assembled With 72 Hydrogen Bonds," Science, Jul. 22, 2011, vol. 333, 436-440.
Sara Pasquale, "Giant Regular Polyhedra From Calixarene Carboxylates and Uranyl," Nature Communications, Apr. 17, 2012, Macmillan Publishers Limited., vol. 758, 1-7.
Christoph Glitz, Enantiomerically Pure [M6L12] or [M12L24] Polyhedra from Flexible Bis(Pyridine) Ligands, Angew. Chem. Int. Ed., 2014, vol. 53, 1693-1698, Wiley-VCH Verlag GmbH & Co.
Bogdon Olenyuk, "Self-Assembly of Nanoscopic Dodecahedra from 50 Predesigned Components," J. Am Chem. Soc. Oct. 22, 1999, vol. 121, 10434-10435.
Kate Harris, "Giant Hollow MnL2n Spherical Complexes: Structure, Functionalisation and Applications," Chem. Commun., 2013, vol. 49, 6703-6712, The Royal Society of Chemistry.
Timothy R. Cook, "Metal-Organic Frameworks and Self-Assembled Supramolecular Coordination Complexes: Comparing and Contrasting the Design, Synthesis, and Functionality of Metal-Organic Metals," Chem. Rev. 2013, vol. 113, 734-777.
Tobias Schroder, "A Self-Assembling Metallosupramolecular Cage Based on Cavitand-Terpyridine Subunits," Tetrahedron Letters, 2008, vol. 49, 5939-5942.

(Continued)

*Primary Examiner* — Pancham Bakshi
(74) *Attorney, Agent, or Firm* — Renner Kenner Greive Bobak Taylor and Weber

(57) ABSTRACT

A process is provided for precise self-assembly and re-arrangement of a three-dimensional terpyridine-based coordination complex. A plurality of terpyridine-containing ligands are reacted with at least one metal ion, in a pre-selected molar ratio, to form a self-assembled three-dimensional terpyridine-based coordination complex having a first configuration. A triggering event, such as exposure to light or dilution, causes the coordination complex to re-arrange to form at least two smaller, substantially identical, three-dimensional terpyridine-based coordination complexes, each having a second configuration that is different from the first configuration. Upon application of a second triggering event, such as concentration, the re-arrangement is reversed.

13 Claims, 12 Drawing Sheets
(12 of 12 Drawing Sheet(s) Filed in Color)

(56) References Cited

OTHER PUBLICATIONS

Chao Wang, "Self Assembly of Giant Supramolecular Cubes With Terpyridine Ligands as Vertices and Metals on Edges," Chem. Sci. 2014, vol. 5, 1221-1226.
Ting-Zheng Xie, "Construction of a Highly Symmetric Nanosphere via a One-Pot Reaction of a Tristerpyridine Ligand with Ru(II)," J. Am. Chem Soc. 2014, vol. 136, 8165-8168.
Anthony Schultz, "Stable, Trinuclear Zn(II)- and Cd(II)-Metallacycles: TWIM-MS, Photophysical Properties, and Nanofiber Formation," Dalton Trans. 2012, vol. 41, 11573-11575.
George R. Newkome, "Self-and Directed Assembly of Hexaruthenium Macrocycles," Angew. Chem. Int. Ed. 1999, vol. 38, 3717-3721.
George R. Newkome, Nanoassembly of a Fractal Polymer: A Molecular "Sierpinski Hexagonal Gasket," Science, Jun. 23, 2006, vol. 312, 1782-1785.
Rajarshi Sarkar, "One-Step Multicomponent Self-Assembly of a First-Generation Sierpinski Triangle: From Fractal Design to Chemical Reality," Angew. Chem. Int. Ed. 2014, vol. 53, 12182-12185.
Jin-Liang Wang, "Stoichiometric Self-Assembly of Shape-Persistent 2D Complexes: A Facile Route to a Symmetric Supramacromolecular Spoked Wheel," J. Am. Chem. Soc. 2011, vol. 133, 11450-11453.
Dip Singh Gill, "Study of the Comparative Salvation Behaviour of Na+ and Cu+ Cations in Acetonitrile + N,N-Dimethylformamide Mixtures at 298.15 K," Dept. of Chemistry, India, Apr. 26, 2004, 59a, 615-620.
Xiaopeng Li, "Separation and Characterization of Metallosupramolecular Libraries by Ion Mobility Mass Spectrometry," Anal. Chem. 2011, vol. 83, 1284-1290.
Sujith Perera, "Hexameric Palladium (II) Terpyridyl Metallomacrocycles: Assembly with 4,4'-Bipyridine and Characterization by TWIM Mass Spectrometry," Angew. Chem. Int. Ed 2010, vol. 49, 6539-6544.
Cherokee S. Hoaglund-Hyzer, "Anhydrous Protein Ions," Chem. Rev., Sep. 25, 1999, vol. 99, 3037-3079.
Erin R. Brocker, "Structures of Metallosupramolecular Coordination Assemblies Can Be Obtained by Ion Mobility Spectrometry—Mass Spectrometry," J. Am. Chem. Soc. 2010, vol. 132, 13486-13494.
Xiaocun Lu, "Probing a Hidden World of Molecular Self-Assembly: Concentration-Dependent, Three-Dimensional Supramolecular Interconversions," J. Am.Chem Soc. 2014, vol. 136, 18149-18155.
Alexandre A. Shvartsburg, "An Exact Hard-Spheres Scattering Model for the Mobilities of Polyatomic Ions," Chem. Phys. Lett., 1996, vol. 261, 86-91.
Martin F. Jarrold, "Peptides and Proteins in the Vapor Phase," Annu. Rev. Phys. Chem. 2000, vol. 51, 179-207.
Alexandre A. Shvartsburg, "Evaluation of Ionic Mobilities by Coupling the Scattering on Atoms and on Electron Density," J. Phys. Chem A, 2000, vol. 104, 6152-6157.
Francesco Lanucara, "The Power of Ion Mobility-Mass Spectrometry for Structural Characterization and the Study of Conformational Dynamics," Nat. Chem., 2014, vol. 6, 281-294.
Yi-Tsu Chan, "Design, Synthesis, and Traveling Wave Ion Mobility Mass Spectrometry Characterization of Iron(II)—and Ruthenium(II)—Terpyridine Metallomacrocycle," J. Am. Chem. Soc., 2011, vol. 133, 11967-11976.
Manik Lal Saha, "Spontaneous and Catalytic Fusion of Supramolecules," Chem. Commun., 2012, vol. 48, 9459-9461.
Makoto Fujita, "On the Structure of Transition-Metal Linked Molecular Squares," Chem. Commun., 1996, 1535-1536.
Tomas Kraus, "Copper(I)-Directed Formation of a Cyclic Pseudorotaxane Tetramer and Its Trimeric Homologue," Angew. Chem. Int. Ed. 2006, vol. 45, 258-261.
Manuela Schweiger, "Solution and Solid State Studies of a Triangle-Square Equilibrium: Anion-Induced Selective Crystallization in Supramolecular Self-Assembly," INorg. Chem. 2002, vol. 41, 2556-2559.
George R. Newkome, "From 1-3 Dendritic Designs to Fractal Supramacromolecular Constructs: Understanding the Pathway to the Sierpinski Gasket," Chem. Soc. Rev., 2015, vol. 44, 3954-3967.
Mathias Nilsson, "The DOSY Toolbox: A New Tool for Processing PFG NMR Diffusion Data," Journal of Magnetic Resonance, 2009, vol. 200, 296-302.
Thalassinos, Konstantinos, "Characterization of Phosphorylated Peptides Using Traveling Wave-Based and Drift Cell Ion Mobility Mass Spectrometry," Anal. Chem., 2009, vol. 81, 248-254.
Francisco A. Fernandez-Lima, "A Study of Ion-Neutral Collision Cross-Section Values for Low Charge States of Peptides, Proteins, and Peptide/Protein Complexes," Int. J. Mass Spectrom. 2010, vol. 298, 111-118.
M.F. Mesleh, "Structural Information From Ion Mobility Measurements: Effects of the Long-Range Potential." J. Phys. Chem, 1996, vol. 100, 16082-16086.

* cited by examiner

PRECISE THREE-DIMENSIONAL SUPRAMACROMOLECULE INTERCONVERSIONS

CROSS-REFERENCE TO RELATED APPLICATIONS

This application claims the benefits of U.S. Provisional Patent Application Nos. 62/110,662, filed Feb. 2, 2015, and 62/164,641, filed May 21, 2015, both of which are incorporated herein by reference.

STATEMENT REGARDING FEDERALLY SPONSORED RESEARCH OR DEVELOPMENT

This invention was made with government support under (CHE-1151991 and CHE-1308307) awarded by the National Science Foundation. The government has certain rights in the invention.

FIELD OF THE INVENTION

The present invention generally resides in the field of supramacromolecules and precise processes involving the interconversion of supramacromolecules into alternate configurations. The present invention also resides in the art of coordination chemistry, employing metal ions and associated coordinating ligands.

BACKGROUND OF THE INVENTION

Nature exhibits highly symmetrical polyhedral cage-like structures at different scales, such as viral capsids, clatherin-coated vesicles, and the protein transport complex, COPII. All are connected mathematically by Archimedean polyhedrons and from a synthetic chemistry perspective, by the common thread of protein complex self-assembly. Inspired by both biomolecules and their underlying geometric principles, chemists have developed routes to create capsule and polyhedral assemblies utilizing hydrogen-bonding or coordination interactions. Replicating large, multi-component, three-dimensional architectures in vitro is synthetically challenging, due in part, to the precise control necessary for building block assembly and the fact that subtle changes in the subunits can give very different results. Notable achievements toward the synthetic construction of very large, cage-like constructs include cuboctahedrons and dodecahedrons (5.2 and 7.5 nm, respectively, based on pulsed gradient spin-echo NMR), rhombicuboctahedrons and sphere-in-sphere rhombicuboctahedrons (5.0 and 6.3 nm, respectively, based on synchrotron X-ray crystal data).

The eloquent architecture of the protein complex COPII and its structural connection to Archimedean polyhedrons provided inspiration for the design and construction of highly symmetric, 3D, supra-molecular structures. The molecular motif and critical parameters of building block preciseness-of-fit and method of connectivity were considered. Ligand-metal-ligand building block connectivity provides desirable synthetic characteristics by facilitating metal coordination sites to act as either vertices or as edges in a contemplated shape. The linearly-coordinated, pseudo-octahedral, <tpy-$M^{2+}$-tpy> complex (where, tpy=[2,2':6',2"] terpyridine) has been demonstrated to be a good option for the fabrication of 2D and 3D supramolecules.

FIG. 1 illustrates the construction of simple and complex 2D polygons including a Sierpinski triangle and gasket, based on single-angle components and derivation of Archimedean polyhedrons using multi-angle, building blocks possessing increasingly greater angles ($\beta$), where the critical dihedral angles within the cuboctahedron are 125° corresponding to $\beta=90°$.

Use of [2,2':6',2"]terpyridine, as a readily available and easily functionalized monomer, has been reported for the self-assembly of numerous 2D, metallomacrocycles including, triangles, hexagons, a Sierpinski gasket, and a Sierpinski triangle, wherein the vertices were connected through terpyridine-based coordination chemistry.

Precise control over the interconversion between different supramolecular assemblies remains a desirable goal.

SUMMARY OF THE INVENTION

In one or more embodiments of the present invention, a process is provided for precise self-assembly and re-arrangement of a three-dimensional terpyridine-based coordination complex. A plurality of terpyridine-containing monomer molecules are reacted with at least one metal ion, in a pre-selected molar ratio, to form a self-assembled three-dimensional terpyridine-based coordination complex having a first configuration. A triggering event, such as exposure to light or dilution, causes the coordination complex to re-arrange to form at least two smaller, substantially identical, three-dimensional terpyridine-based coordination complexes, each having a second configuration that is different from the first configuration.

Embodiments of the present invention further provide a process for precise self-assembly and re-arrangement of a three-dimensional terpyridine-based coordination complex, the process comprising the steps of reacting a plurality of terpyridine-containing monomer molecules with at least one metal ion, wherein the metal is selected from the group consisting of $Fe^{+2}$, $Ru^{+2}$, $Os^{+2}$, $Ir^{+2}$, $Zn^{+2}$, $Sn^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$, and combinations thereof, in a pre-selected molar ratio, to form a self-assembled three-dimensional terpyridine-based coordination complex having a first configuration; and exposing said coordination complex to a triggering event, whereupon said coordination complex re-arranges to form at least two smaller, substantially identical, three-dimensional terpyridine-based coordination complexes, each having a second configuration that is different from the first configuration.

Embodiments of the present invention further provide a process for precise self-assembly and re-arrangement of a three-dimensional terpyridine-based coordination complex, the process comprising the steps of reacting a plurality of bridged anthracene tetrakis(terpyridine) monomer molecules with at least one metal ion, wherein the metal is selected from the group consisting of $Fe^{+2}$, $Ru^{+2}$, $Os^{+2}$, $Ir^{+2}$, $Zn^{+2}$, $Sn^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$, and combinations thereof, in a pre-selected molar ratio, to form a self-assembled three-dimensional terpyridine-based coordination complex having a first configuration; and exposing said coordination complex to a pre-selected triggering event, whereupon said coordination complex re-arranges to form at least two smaller, substantially identical, three-dimensional terpyridine-based coordination complexes, each having a second configuration that is different from the first configuration.

Embodiments of the present invention further provide a cuboctahedral terpyridine-based supramacromolecule comprising a plurality of bridged anthracene tetrakis(terpyridine) molecules complexed to a plurality of metal ions, and wherein the diameter of the supramacromolecule is at least about 6 nanometers.

Embodiments of the present invention further provide a cuboctahedral terpyridine-based supramacromolecule that is formed by combining a plurality of bridged anthracene tetrakis(terpyridine) molecules with a plurality of metal ions selected from the group consisting of $Fe^{+2}$, $Ru^{+2}$, $Os^{+2}$, $Ir^{+2}$, $Zn^{+2}$, $Sn^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$, and combinations thereof, in a molar ratio of about 1:2.

Embodiments of the present invention further provide a metallodendrimer that is formed by a process that includes the step of combining a plurality of bridged anthracene tetrakis(terpyridine) molecules with a plurality of metal ions selected from the group consisting of $Fe^{+2}$, $Ru^{+2}$, $Os^{+2}$, $Ir^{+2}$, $Zn^{+2}$, $Sn^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$, and combinations thereof, in a molar ratio of about 1:2.

Embodiments of the present invention further provide a supramolecular capsule that is formed by combining a plurality of bridged anthracene tetrakis(terpyridine) molecules with a plurality of metal ions selected from the group consisting of $Fe^{+2}$, $Ru^{+2}$, $Os^{+2}$, $Ir^{+2}$, $Zn^{+2}$, $Sn^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$, and combinations thereof, in a molar ratio of about 1:2.

Embodiments of the present invention further provide a method of releasably encapsulating a payload in a supramolecular capsule, the method comprising the steps of providing a solution comprising a payload, a carrier, and a first three-dimensional terpyridine-based coordination complex having a first configuration, wherein the complex is formed by reacting a plurality of terpyridine-containing monomer molecules with at least one metal ion, wherein the metal is selected from the group consisting of $Fe^{+2}$, $Ru^{+2}$, $Os^{+2}$, $Ir^{+2}$, $Zn^{+2}$, $Sn^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$, and combinations thereof, in a preselected molar ratio, wherein the coordination complex is present in an amount of at least about $1 \times 10^{-4}$ mmoL/mL; diluting said solution by a factor of at least about 10 with a solvent, wherein said step of diluting causes said coordination complex to re-assemble into multiple coordination complexes that are smaller relative to said first coordination complex, and that have a second configuration, each smaller coordination complex effectively encapsulating said payload; and optionally, concentrating said solution by a factor of at least 10, wherein said step of concentrating said solution results in the re-arrangement of said multiple smaller coordination complexes into said first coordination complex, thereby releasing said payload into said solution.

Embodiments of the present invention provide a process for precise self-assembly and re-arrangement of a three-dimensional terpyridine-based coordination complex, the process comprising the steps of: reacting a plurality of tristerpyridine-based monomer molecules with at least one metal ion, wherein the metal is selected from the group consisting of $Fe^{+2}$, $Ru^{+2}$, $Os^{+2}$, $Ir^{+2}$, $Zn^{+2}$, $Sn^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$, and combinations thereof, in a molar ratio of about 2:3, to form a self-assembled three-dimensional terpyridine-based coordination complex having a first configuration; and diluting said coordination complex in a suitable solvent, by a factor of at least about 10, whereupon said coordination complex re-arranges to form at least two smaller, substantially identical, three-dimensional terpyridine-based coordination complexes, each having a second configuration that is different from the first configuration.

Embodiments of the present invention provide a method for preparing a tetrahedral terpyridine-based metallomacrocycle, the method comprising the steps of reacting a plurality of tristerpyridine monomer molelcules with at least one metal ion, wherein the metal is selected from the group consisting of $Fe^{+2}$, $Ru^{+2}$, $Os^{+2}$, $Ir^{+2}$, $Zn^{+2}$, $Sn^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$, and combinations thereof, in a molar ratio of about 2:3, to form a self-assembled three-dimensional terpyridine-based coordination complex having a first configuration; and diluting said coordination complex in a suitable solvent, by a factor of at least about 10, whereupon said coordination complex dis-assembles to form at least two smaller, substantially identical, tetrahedral terpyridine-based coordination complexes.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF ILLUSTRATIVE EMBODIMENTS

The present invention provides terpyridine-based supramacromolecules, methods of making them, and methods of reversibly and precisely altering their configuration and size.

One or more embodiments of the present invention are directed to supramacromolecules that comprise a precise polyhedral arrangement of three-dimensional metal coordination complexes. The supramacromolecules are monodisperse, highly symmetric complexes, obtainable via single-step, quantitative self-assembly.

In one or more embodiments, the metal atoms are selected from metals that are capable of coordinating with a plurality of ligands.

In one or more embodiments, the supramacromolecule is a cuboctahedral terpyridine-based supramacromolecule comprising a plurality of bridged anthracene tetrakis (terpyridine) molecules complexed to a plurality of metal ions. In one or more embodiments, the diameter of the supramacromolecule is at least about 4 nanometers. In one or more embodiments, the diameter of the supramacromolecule is at least about 5 nanometers, in other embodiments, at least about 6 nanometers. Embodiments of the invention provide a three-dimensional six nanometer (nm) cuboctahedral metallosphere.

Figure 1:
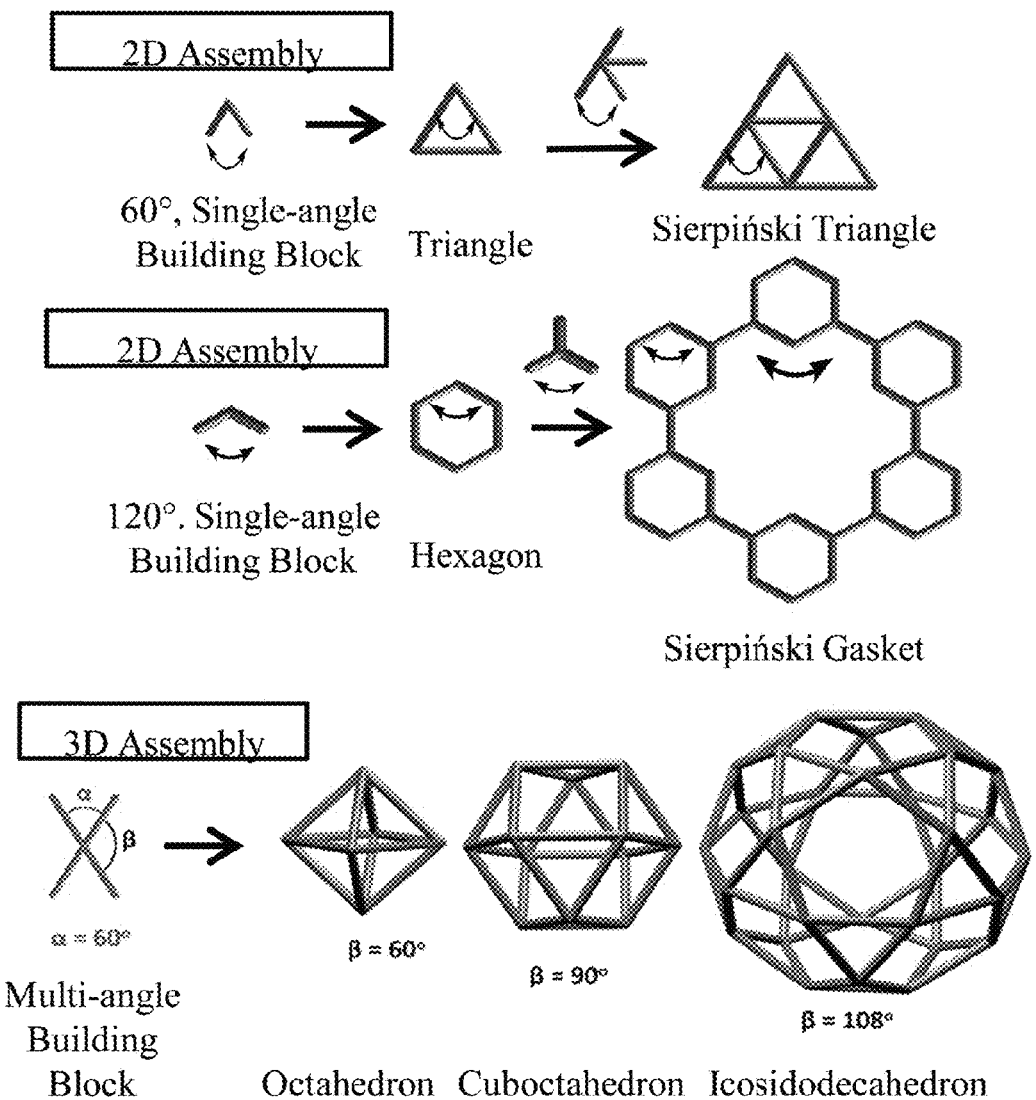
FIG. 1 provides schemes of the construction of simple and complex 2D polygons including a Sierpinski triangle and gasket, based on single-angle components and derivation of Archimedean polyhedrons using multi-angle, building blocks possessing increasingly greater angles ($\beta$), where the critical dihedral angles within the cuboctahedron are 125° corresponding to $\beta=90°$.

Advantageously, the cuboctahedral supramacromolecule resembles a classic Archimedean polyhedron—exhibiting two or more nonintersecting regular convex polygons arranged such that all sides are of equal length. In one or more embodiments, the building block for this semi-regular polygon, i.e. monomer, is an X-shaped molecular building block that can be mapped onto the vertices of a cuboctahedron and impart the desired angles, α and β, with values of 60° and 90°, respectively (FIG. 1). Notably, the appropriate molecular molecular building block may create a cumulative shape-persistent memory effect that translates to the subsequent architectural assembly.

In one or more embodiments, the cuboctahedral supramacromolecule may be described by 24 edges and 12 vertices forming the basis of 14 total faces comprised of 8 triangles and 6 squares, all predicated on 24 dihedral angles equal to about 125°.

In other embodiments, the supramacromolecule is a tetrahedral terpyridine-based coordination complex. Multitopic ligands form the vertices and metal-ligand connectivity forms the sides, and shown in FIG. 5.

The supramacromolecules of the present invention may be further described by reference to the monomer units and metals that make up the supramacromolecules.

One or more embodiments are directed to supramacromolecules comprising poly-ligand monomers bound through coordination to metal ions. To the extent that the supramacromolecules may be formed by self-assembly, the supramacromolecules may be referred to as supramolecular assemblies. Conceptually, the poly-ligand monomers may be considered to be the building blocks of the supramacromolecules.

For purposes of economy, an "L" is used in the accompanying figures to indicate the poly-ligand monomer. However, for a more detailed discussion of the poly-ligand monomer, it is helpful to describe the poly-ligand monomer as including an anchoring group that may be referred to as the vertex of the monomer (V), and a plurality of coordinating moieties that are capable of coordinating to metal atoms, and that may be referred to as ligands (L). That is, while in the attached figures "L" and "Ligand" refer to the poly-ligand monomer, within this detailed description, "L" refers to the coordinating moieties of the poly-ligand monomer.

The ligands may be tethered to the vertex directly, or via a spacer moiety (S). In one or more embodiments, the ligands are terpyridine-based ligands, i.e. substituted or un-substituted terpyridinyl groups. In one or more embodiments, all of the ligands are identical.

In one or more embodiments, the poly-ligand monomer may be defined by the formula $$V\text{-}(L)n$$

where V is a polyvalent organic group, each L is individually a ligand group, and n is an integer of at least 2. In one or more embodiments, n is 3. In one or more embodiments, n is 4.

In one or more embodiments, where the poly-ligand monomer includes a spacer group (S), the poly ligand monomer may be defined by the formula

where S is a divalent organic group, and V, L, and n are as described above.

Generally, the ligands are selected from organic groups that include one or more sites capable of coordinating a metal atom. The ligands are typically covalently bonded to the anchoring group, or to the spacer group, if present. Examples of ligand groups include pyridines, bipyridines, terpyridines, pyrroles, polypyrroles, thiophenes, polythiophenes, phosphines, polyphosphines, isoxazoles, oxazoles, pyrimidines, polypyrimidines, pyridazines, poly pyridazines, polyoxazoles, thiazoles, and polythiazoles, and substituted forms thereof. In one or more embodiments, the ligands are substituted or unsubstituted pyridines, bipyridines, or terpyridines. In one or more embodiments, the ligands are substituted or unsubstituted terpyridinyl ligands.

The optional spacer groups may be selected from divalent organic groups, and may also be referred to as linking groups, in that they link the ligands to the anchoring group. Spacer groups may be saturated or unsaturated hydrocarbon groups. Spacer groups may contain heteroatoms.

Generally, the anchoring group is an organic moiety that is capable of forming covalent bonds with two or more spacer or ligand groups. Examples of anchoring groups include benzene, anthracene, bridged-anthracene, triptycene, and substituted forms thereof.

In one or more embodiments, the shape of the supramacromolecule may be dictated by the anchoring group of the poly-ligand monomers. In one or more embodiments, the anchoring group forms the vertices of the supramacromolecular structure. By carefully selecting the anchoring group of the poly-ligand monomer, the relative angles of the ligand groups may selected, and thereby the shape of the supramacromolecule. This will become evident as described in more detail hereinbelow.

In one or more embodiments, the anchoring group is substantially planar. Examples of substantially planar anchoring groups include benzene. In these embodiments, the dimensional structure of the poly-ligand monomer may be described with reference to the angles at which the ligands extend from the anchoring group relative to the other ligands.

In one or more embodiments, the ligand groups extend from the anchoring group at an angle with respect to adjacent ligand groups, and that angle may be referred to as a planer angle. These types of angles are further described in co-pending U.S. patent application Ser. No. 15/007,456, filed on Jan. 27, 2016, which is incorporated by reference herein. In one or more embodiments, each ligand extends from the anchoring group at a planar angle of from about 60 to about 135°, with respect to at least one adjacent ligand. Specific examples of planer angles between adjacent ligands include about 60, in other embodiments, about 90, in other embodiments, about 135°.

In one or more embodiments, the poly-ligand monomer includes two or more substituted or unsubstituted terpyridinyl ligands. In one or more embodiments, the poly-ligand monomer includes three substituted or unsubstituted terpyridinyl ligands, and thus may be referred to as a tristerpyridinyl monomer. In one or more embodiments, the monomer is 1,2,3-trimethoxy-4,5,6-tris[p-(4'-terpyridinyl)phenyl]benzene, or a planar substituted form thereof.

In one or more embodiments, where the vertex of the poly-ligand monomer is a benzene group, the poly-ligand monomer may be represented by the following structure:

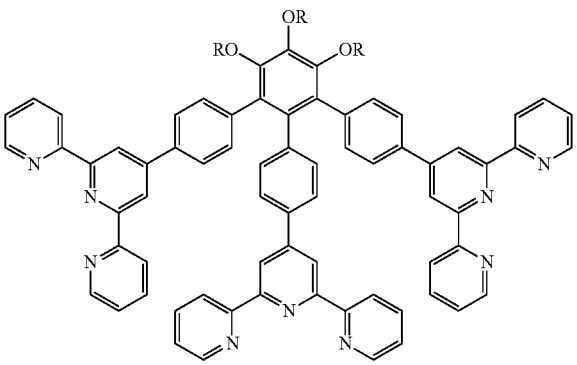

where each R is independently hydrogen or a monovalent organic group. In one or more embodiments, each R is independently selected from alkyl groups. Examples of alkyl groups include, but are not limited to, methyl, ethyl, propyl, butyl, pentyl, hexyl, heptyl, octyl, nonyl, decyl, isopropyl, isobutyl, sec-butyl, and tert-butyl neopentyl, phenyl, benzyl, and napthyl. In one or more embodiments, oxygen may instead be sulfur, nitrogen, or phosphorus.

In other embodiments, the anchoring group is non-planar. Examples of non-planar anchoring groups include bridged anthracene. In these embodiments, the poly-ligand monomer is also non-planar, and may be described as having one plane that passes through the anchoring group and one or more of the ligands, and another plane that passes through the anchoring group and another of the ligands. The angle between the planes may be referred to as a dihedral angle.

In one or more embodiments, the poly-ligand monomer may be characterized by having a dihedral angle of from about 108 to about 130°. Specific examples of dihedral angles include 120, 125 and 127°.

The bridged anthracene anchoring group may be represented by the following structure:

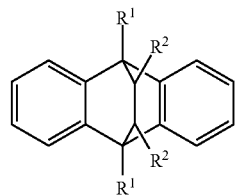

where each $R^1$ is individually a hydrogen atom or an alkyl group, and each $R^2$ is individually a monovalent organic group, or where two $R^2$ groups combine to form a cyclic divalent organic group. Bridged anthracenes are further described in U.S. Pat. No. 3,678,072, which is incorporated by reference herein.

In one or more embodiments, the anchoring group is a bridged anthracene and the ligands are terpyridinyl, and the poly-ligand monomer may be represented by the following structure:

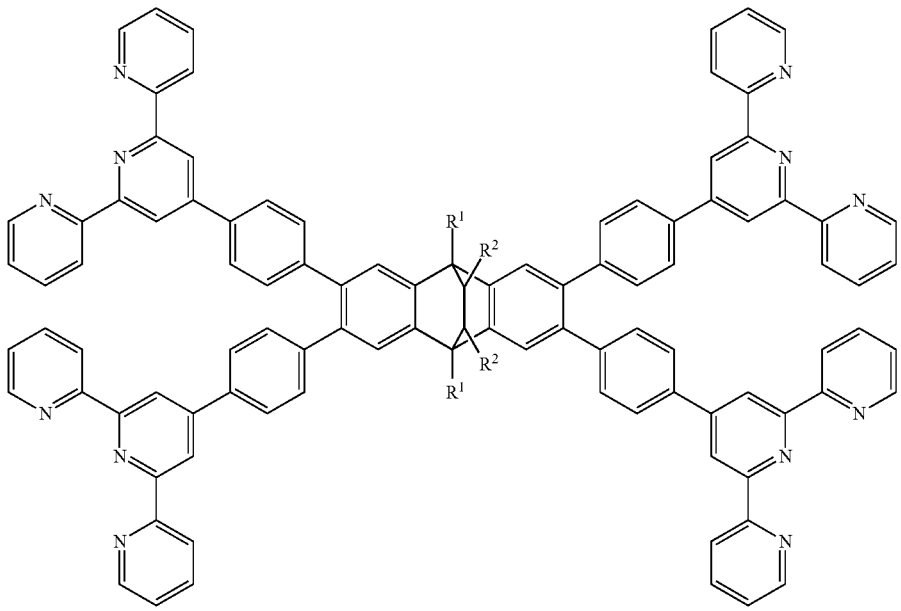

where each $R^1$ and $R^2$ are as described above. In these or other embodiments, the dihedral angle is about 125°.

Advantageously, a novel ethano-bridged anthracene tetrakis(terpyridine) molecule is provided herein, which may be denoted 2,3,6,7-tetrakis(terpyridine)-9,10-ethanoanthracene. In one or more embodiments, the 2,3,6,7-tetrakis(terpyridine)-9,10-ethanoanthracene may be represented by the following structure:

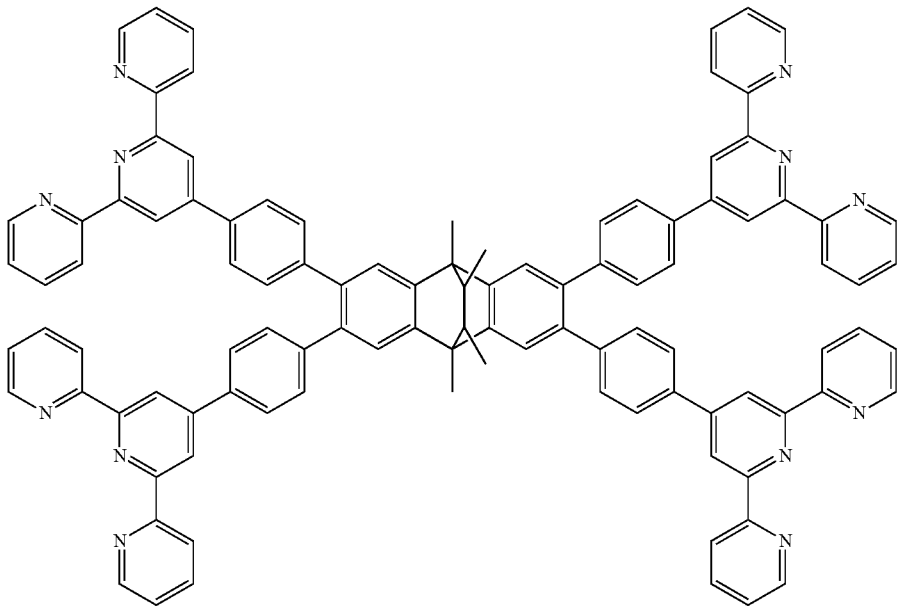 [SMILES: CC1C(C)C2(C)c3cc(-c4ccc(-c5cc(-c6ccccn6)nc(-c6ccccn6)c5)cc4)c(-c4ccc(-c5cc(-c6ccccn6)nc(-c6ccccn6)c5)cc4)cc3C1(C)c1cc(-c3ccc(-c4cc(-c5ccccn5)nc(-c5ccccn5)c4)cc3)c(-c3ccc(-c4cc(-c5ccccn5)nc(-c5ccccn5)c4)cc3)cc12]

In these or other embodiments, the dihedral angle is about 125°.

In one or more embodiments, a poly-ligand monomer with a bridged anthracene group may be represented by the following structure:

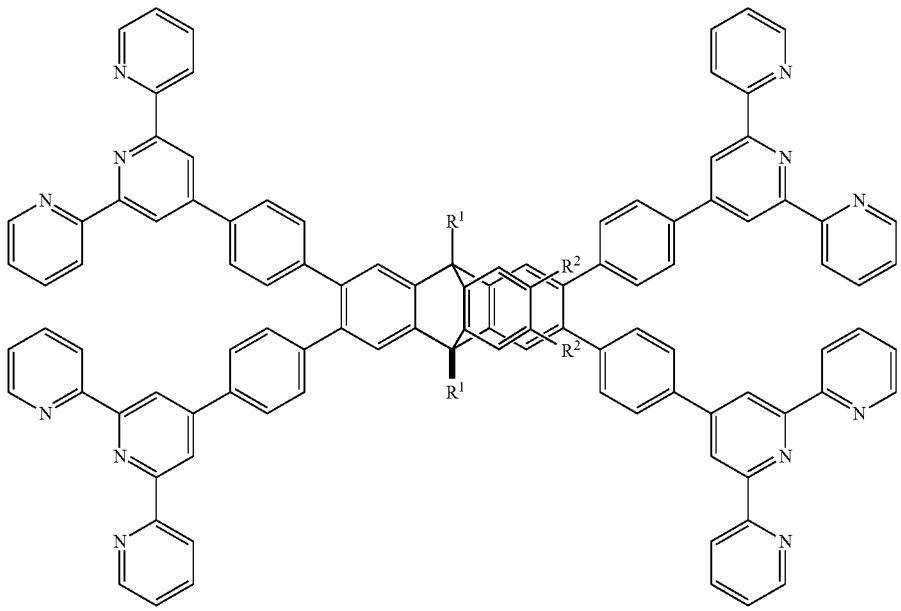

where each R¹ and R² are as described above. In these or other embodiments, the dihedral angle is about 125°.

In one or more embodiments, a poly-ligand monomer with a triptycene anchoring group may be represented by the following structure:

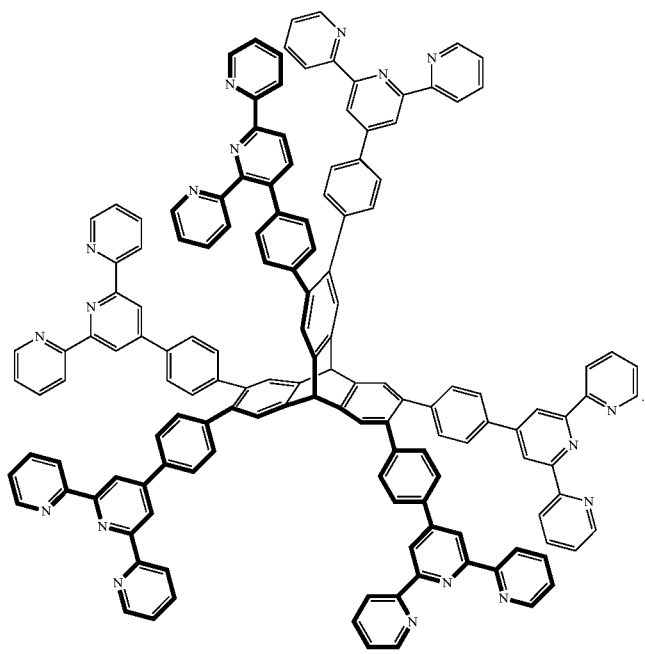

In these or other embodiments, the dihedral angle is about 125°.

In any of the above structures, hydrogen atoms could be substituted with appropriate functional groups. The functional groups may include heteroatoms, and are not particularly limited, so long as they do not prevent or inhibit the self-assembly of the supramacromolecule. Examples of appropriate functional groups include alkyl chains, molecular antennas, and dendrimers.

In one or more embodiments, the multiligand monomer is 2,3,6,7,14,15-hexa(4-terpyridinylphenyl)triptycene. In this or other embodiments, one or two of the terpyridine ligands may be complexed to a secondary terpyridine-based metal coordination complex, and that secondary complex may be functionalized.

Figure 10:
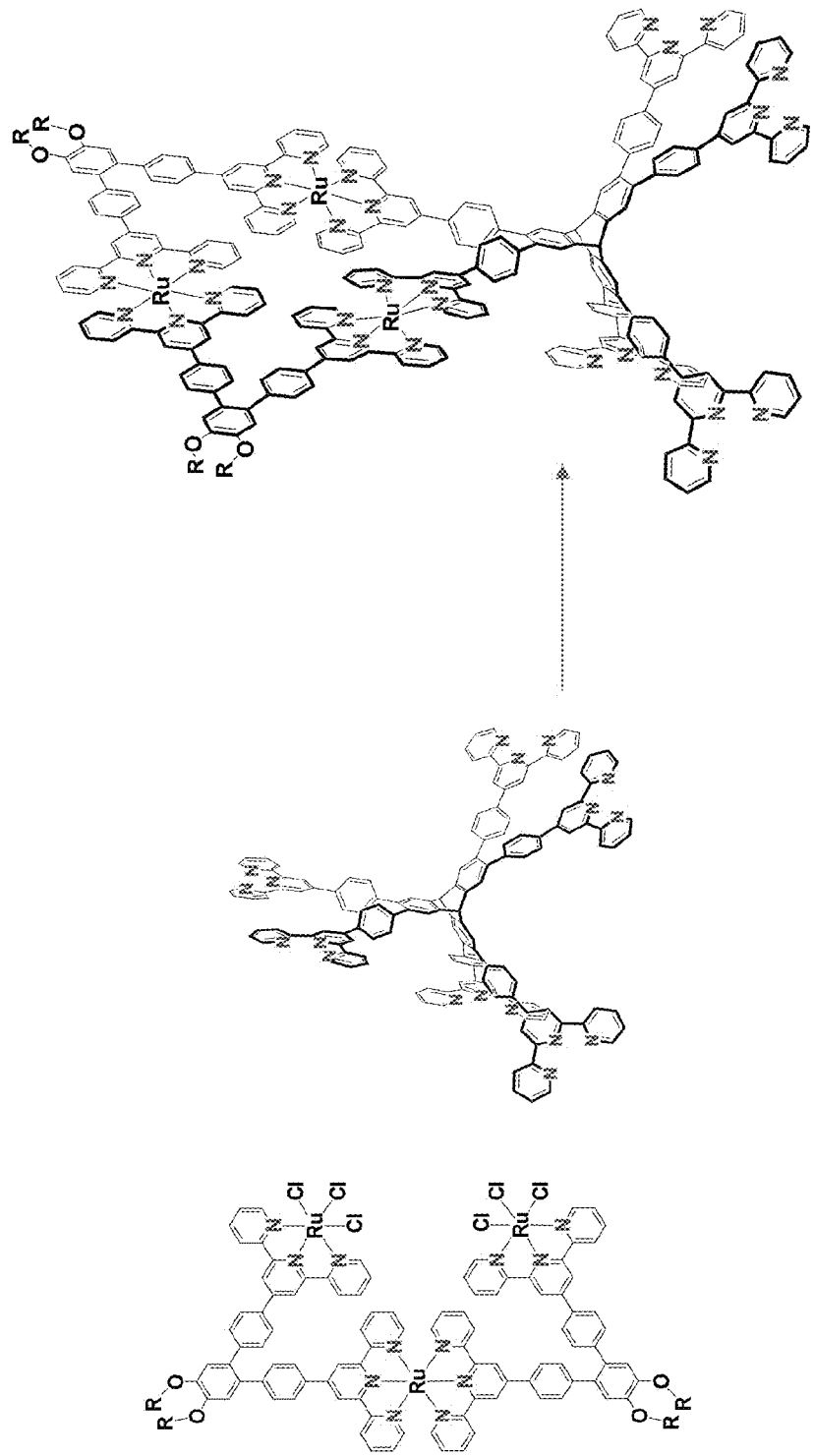
FIG. 10 provides a scheme for the assembly of an embodiment of a hexa(terpyridinyl) monomer wherein two of the terpyridinyl ligands are complexed via metal coordination to an R-functionalized bis-terpyridinyl dimer metal complex.

For example, FIG. 10 provides a scheme for the assembly of an embodiment of a hexa(terpyridinyl) monomer wherein two of the terpyridinyl ligands are complexed via metal coordination to a functionalized (indicated by R) bis-terpyridinyl dimer metal complex. The R groups are not particularly limited, so long as they do not prevent or inhibit the self-assembly of the supramacromolecule. In one or more embodiments, each R is as described above. In one or more embodiments, each R is selected from alkyl groups.

Figure 11:
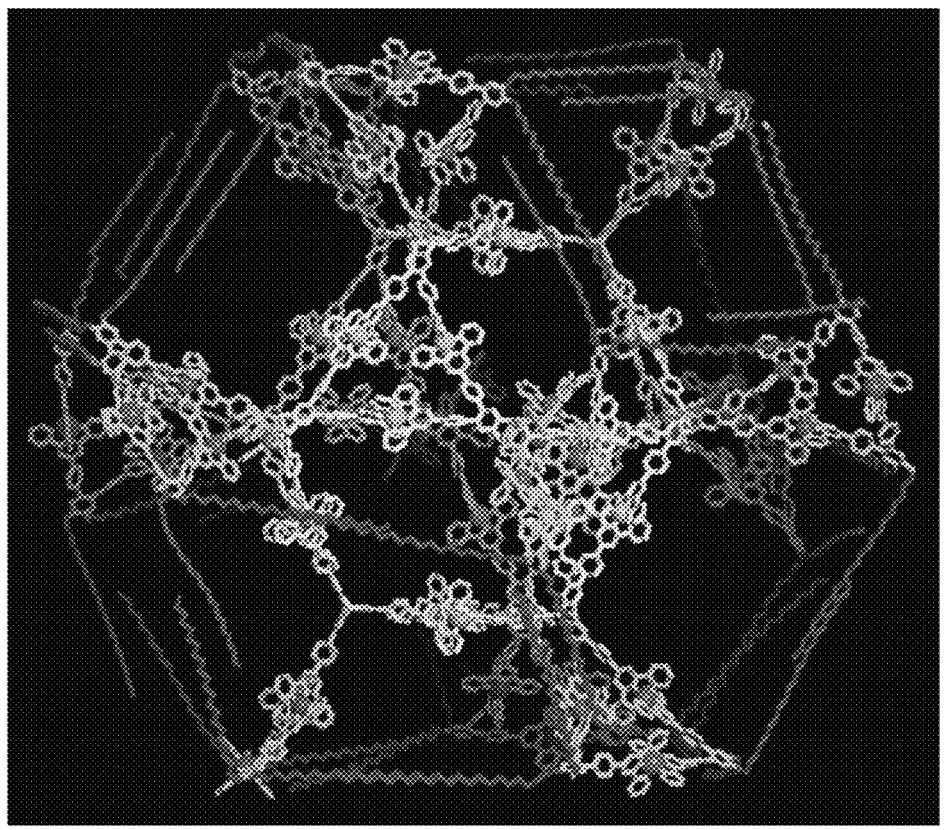
FIG. 11 provides a 3-D diagram of an embodiment of the functionalized hexa(terpyridinyl) coordination complex monomer of FIG. 10, assembled into a cuboctahedral supramacromolecules, where the R groups are shown as blue lines, and represent alkyl chains.

FIG. 11 provides a 3-D diagram of an embodiment of the functionalized hexa(terpyridinyl) coordination complex monomer of FIG. 10, assembled into a cuboctahedral supra-macromolecules, where the R groups are shown as blue lines, and represent alkyl chains.

Figure 12:
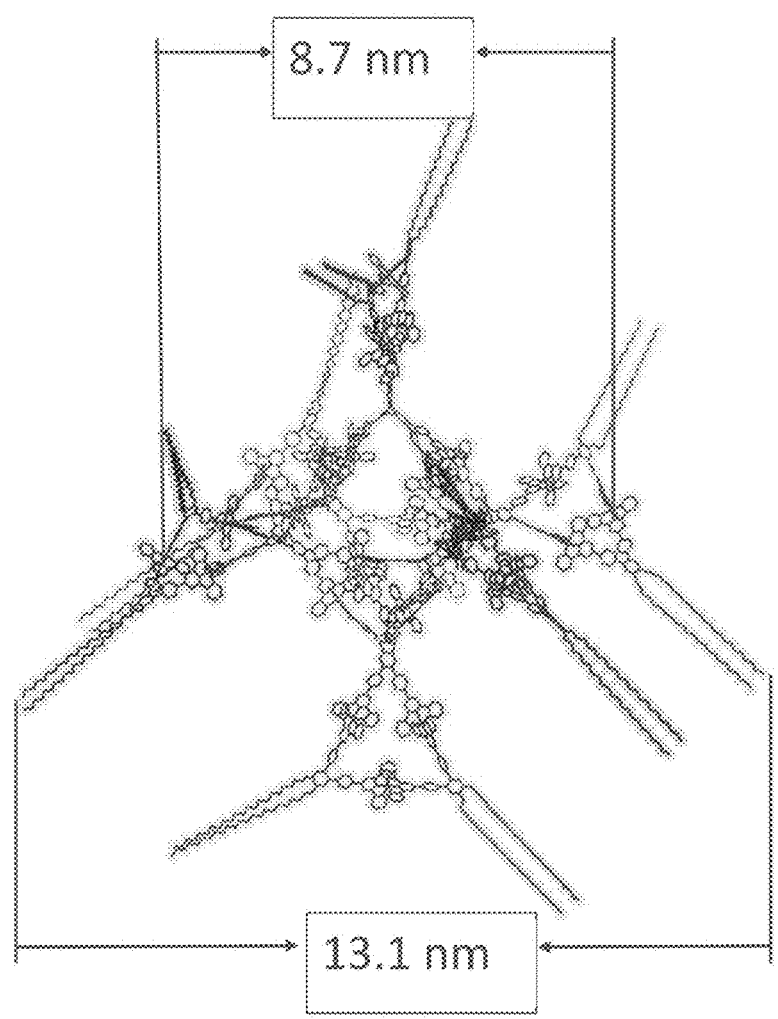
FIG. 12 provides a 3-D diagram of an embodiment of the octahedral supramacromolecule that may result from the re-arrangement of the cuboctahedral supramacromolecule of FIG. 11, where the octahedral complex is shown in blue, the bis-terpyridinyl metal complex and R groups (alkyl chains) are shown in red.

FIG. 12 provides a 3-D diagram of an embodiment of the octahedral supramacromolecule that may result from the re-arrangement of the cuboctahedral supramacromolecule of FIG. 11, where the octahedral complex is shown in blue, the bis-terpyridinyl metal complex and R groups (alkyl chains) are shown in red.

In one or more embodiments, a plurality of poly-ligand monomer molecules are coordinated to metal ions. Suitable metal ions should be kinetically Suitable metal ions include metal ions with an oxidation state of +2. Suitable metal ion with an oxidation state of +2 include $Fe^{+2}$, $Ru^{+2}$, $Os^{+2}$, $Ir^{+2}$, $Zn^{+2}$, $Sn^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$, and combinations thereof. In one or more embodiments, the metal ion is selected from the group consisting of $Zn^{+2}$, $Sn^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$ and combinations thereof. In one or more embodiments, the metal ion is selected from the group consisting of $Fe^{+2}$, $Ru^{+2}$, $Os^{+2}$, $Ir^{+2}$, $Zn^{+2}$, $Cd^{+2}$ and combinations thereof.

In one or more embodiments, the metal ions are typically introduced to the poly-ligand monomers as a salt. Suitable counter ions may be selected from $Br^-$, $I^-$, $ClO_4^-$, $PF_6^-$, $PF_4^-$, carboxylic acids, polycarboxylic acids, triflate, bis[2,2':6',2"]terpyridine-$(CO_2^-)_n$, and dendrimers with surface carboxylates.

Advantageously, supramacromolecules of the present invention may be prepared by self-assembly. In one or more embodiments, a three-dimensional terpyridine-based coordination complex may be prepared by a process comprising the steps of reacting a plurality of terpyridine-based poly-ligand monomer molecules with at least one metal ion, wherein the metal is selected from the group consisting of $Fe^{+2}$, $Ru^{+2}$, $Os^{+2}$, $Ir^{+2}$, $Zn^{+2}$, $Sn^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$, and combinations thereof, in a suitable solvent, and in a pre-selected molar ratio, to form a self-assembled three-dimensional terpyridine-based coordination complex having a first configuration.

Suitable solvents include those in which the metal ion-counter ion pair and the poly-ligand monomer are soluble. Specific examples of suitable solvents include MeOH, $CHCl_3$, and combinations thereof to ensure the solubilization of reagents.

Advantageously, the molar ratio of the monomer molecules to metal ions may be selected to determine the configuration of the supramacromolecule. In one or more embodiments, the molar ratio of the monomer molecules to metal ions is about 1:2. In other embodiments, the molar ratio of the monomer molecules to metal ions is about 2:3. The anchoring group of the monomer, as well as the planar and dihedral angles, may also be selected to determine the configuration of the supramacromolecule.

The supramacromolecule may be characterized as a polyhedron. In one or more embodiments, the polyhedron is an Archimedean polyhedron. Archimedean polyhedrons include polyhedrons with sides made of two or more different polygons, meeting at identical vertices. Specific examples of polyhedrons include truncated tetrahedrons, cuboctahedrons, truncated cubes, truncated octahedrons, rhombicuboctahedrons, truncated cuboctahedrons, snub cubes, icosidodecahedrons, truncated icosahedrons, rhombicosidodecahedrons, truncated icosidodecahedrons, and snub dodecahedrons.

In one or more embodiments, the supramacromolecule may be described as a polyhedron with the edges, or sides, of the polyhedron formed from two coordinated ligands bound to a single metal ion, with the anchoring group forming the vertices of the polyhedron.

Figure 2:
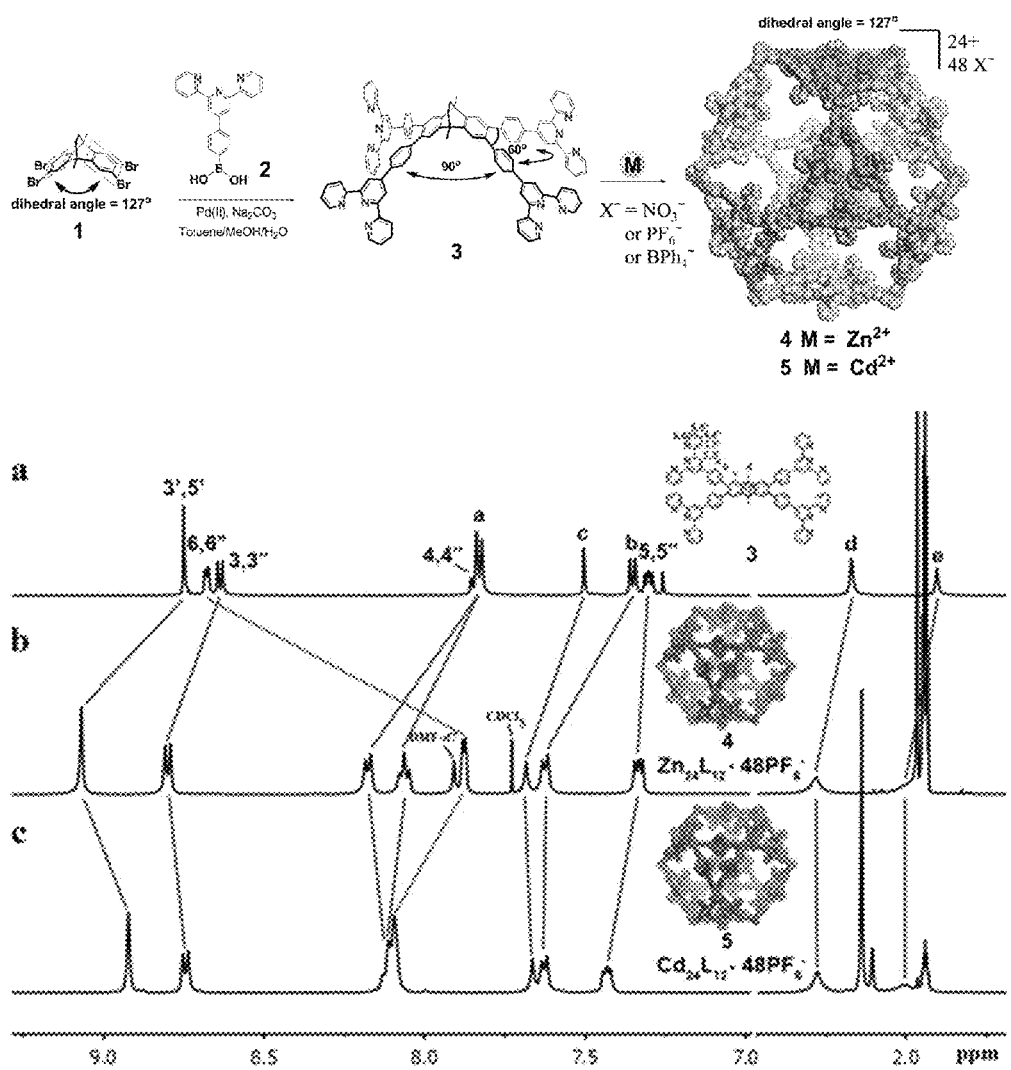
FIG. 2 provides a scheme for the synthesis of the ethano-bridged, tetrakis(terpyridine) monomer 3 and the $Zn^{2+}$- and $Cd^{2+}$-based, cuboctahedra 4 and 5, respectively. The critical dihedral angle (127°) depicted for 1 is translated and instilled into tetrakisterpyridine monomer 3 and the resulting cages 4 and 5. $^1$H NMR spectra (500 MHz, 300 K) of monomer 3 (a) obtained in $CDCl_3$ and complexes 4 (b) and 5 (c) obtained in $CD_3CN$ and DMF-$d_7$ (4:1, v/v).

In one or more embodiments, a 9,10-bridged anthracene monomer having a plurality of terpyridine ligands may be complexed with a plurality of metal ions. In one or more embodiments, a 9,10-bridged anthracene monomer having directed substituted terpyridine connectors may be complexed with a plurality of metal ions in a ratio of 1:2, as shown in FIG. 2, to form a cuboctahedral supramacromolecule.

In one or more embodiments, a three-dimensional terpyridine-based coordination complex may be prepared by a process comprising the steps of reacting a plurality of bridged anthracene tetrakis(terpyridine) molecules with at least one metal ion, wherein the metal is selected from the group consisting $Fe^{+2}$, $Ru^{+2}$, $Os^{+2}$, $Ir^{+2}$, $Zn^{+2}$, $Sn^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$, and combinations thereof, in a suitable solvent, and in a preselected molar ratio, to form a self-assembled three-dimensional terpyridine-based coordination complex having a cuboctahedral configuration.

The present invention further provides a method for preparing a tetrahedral terpyridine-based metallomacrocycle. In one or more embodiments, the method comprises the step of reacting a plurality of tristerpyridine monomer molecules with a plurality of metal ions. The metal ions may be selected from the group consisting of $Fe^{+2}$, $Ru^{+2}$, $Os^{+2}$, $Ir^{+2}$, $Zn^{+2}$, $Sn^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$, and combinations thereof. The monomer molecules and metal ions are combined in a molar ratio of about 2:3, to form a self-assembled three-dimensional terpyridine-based coordination complex having a first configuration. In one or more embodiments, the first configuration may be characterized as a bis-rhombus. Upon diluting the solution of the bis-rhombus supramacromolecule coordination complex in a suitable solvent, by a suitable dilution factor, the coordination complex dis-assembles to form at least two smaller, substantially identical, three-dimensional terpyridine-based coordination complexes, each having a second configuration that is different from the first configuration. In one or more embodiments, the second configuration may be characterized as tetrahedral.

In one or more embodiments, the suitable dilution factor to achieve substantially complete re-arrangement from a bis-rhombus coordination complex to two smaller, identical-to-each-other tetrahedral coordination complexes is at least about 2, in other embodiments, at least about 2.5, in other embodiments, at least about 3, in other embodiments, at least about 5, in other embodiments, at least about 6, in other embodiments, at least about 10, in other embodiments, at least about 15, in other embodiments, at least about 20, in other embodiments, at least about 24.

Figure 6:
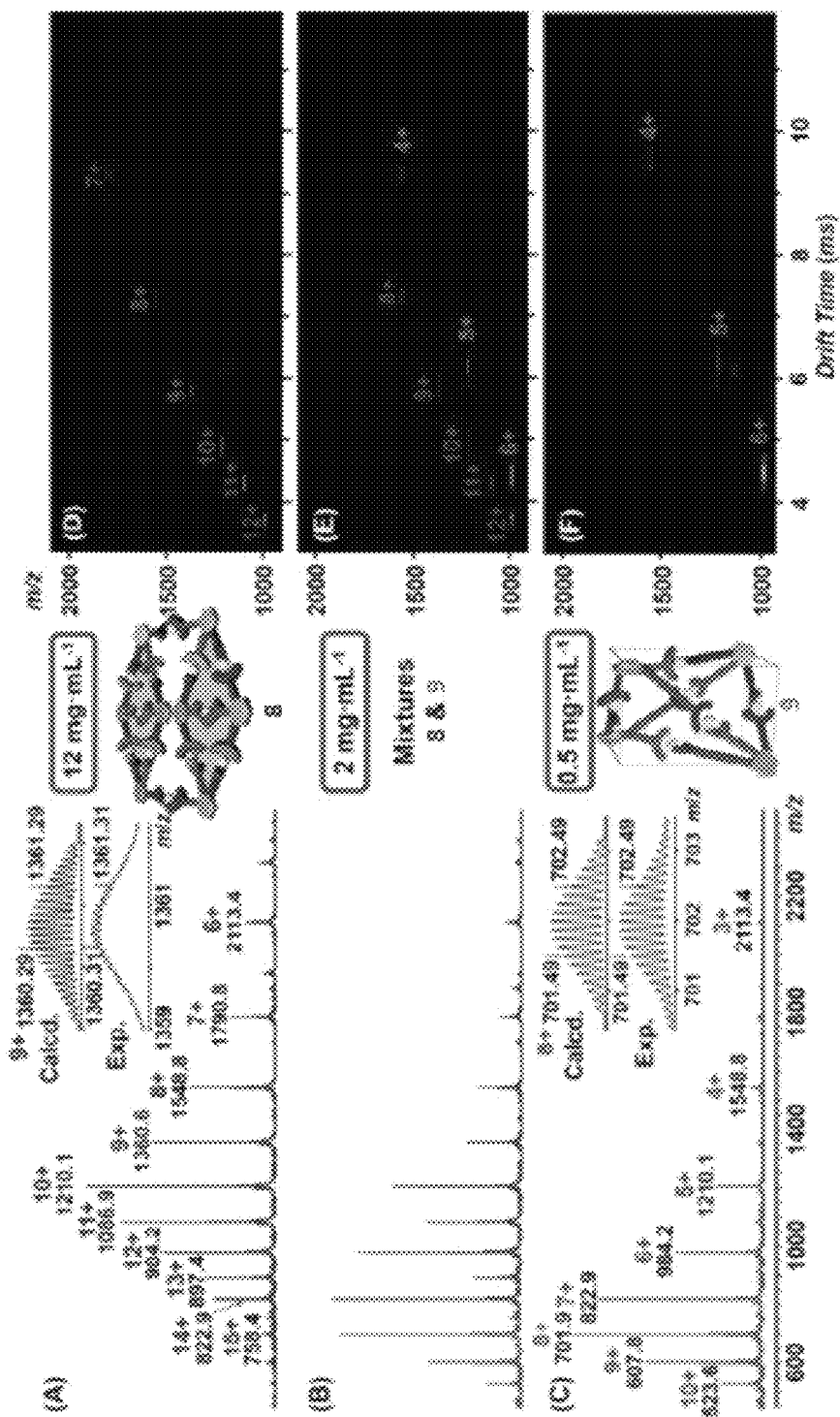
FIG. 6 provides a chart of the ESI-MS of (A) bis-rhombus 2 (12 mg·mL⁻¹ in MeCN), (B) mixture of 8 and 9 (2 mg·mL⁻¹ in MeCN) and (C) tetrahedron 9 (0.5 mg·mL⁻¹ in MeCN); 2D ESI-TWIM-MS plot (m/z vs. drift time) for (D) bis-rhombus 2 (12 mg·mL⁻¹ in MeCN), (E) mixture of 8 and 9 (2 mg·mL⁻¹ in MeCN) and (F) tetrahedron 9 (0.5 mg·mL⁻¹ in MeCN). Charge states of intact assemblies are marked.

Alternately, the concentration change triggering event for the re-arrangement from bis-rhombus to tetrahedral may be described with reference to actual concentration. In one or more embodiments, the self-assembly method described above results in a solution of exclusively bis-rhombus coordination complexes at a concentration of about 12 mg/mL (see FIG. 6), a mixture of bis-rhombus and tetrahedral coordination complexes is obtained when solvent is added to reduce the original concentration of bis-rhombus coordination complex to about 2 mg/mL. Complete re-arrangement to tetrahedral coordination complexes is achieved when additional solvent is added to reduce the original concentration of bis-rhombus coordination complex to about 0.

As alluded to above, it has been advantageously discovered that when a solution of a terpyridine-based coordination complex having a first configuration is subjected to a triggering event such as dilution, the triggering event can cause the coordination complex to re-arranged in a precise manner. For purposes of this specification, unless otherwise indicated, the configuration of the coordination complex that is first formed when poly-ligand monomer molecules are reacted with metal ions is referred to as the first configuration. The configuration of the coordination complex(es) that are formed when the first configuration is subjected to a triggering event and consequently re-arranges is referred to as the second configuration.

Advantageously, it has been found that the configuration of certain supramacromolecules is environmentally sensitive, and may be controlled by careful application of triggering events. Particularly, the coordination complex may respond to triggering events such as changes in temperature, pressure, concentration, and even exposure to certain wavelengths of light radiation or radiation. In one or more embodiments, the response is a fusion- or fission-like re-arrangement that produces coordination complex(es) having a different configuration. In fission-like re-arrangements, the result of the re-arrangement may be the formation of two or more, smaller, supramacromolecules from each original supramacromolecule. The result of a fusion-like re-arrangement may be the formation of one, larger, supramacromolecule from the combination of two or more smaller supramacromolecules. Notably, the re-arrangement is precise and predictable. In one or more embodiments, the re-arrangement is reversible.

In one or more embodiments, the second configuration may be a precise rearrangement of the first configuration, wherein there is a whole number ratio of the number of metal ions and poly-ligand monomers in the first configuration and the number of metal ions and poly-ligand monomers in the second configuration. For example, in one or more embodiments, two or more supramacromolecules may combine, and the new configuration may have twice as many metal ions and poly-ligand monomers as that of the original configuration. It should be noted that this combination differs from typical "self-assembly" in that the configuration, i.e. polygonal arrangement, changes. In these or other embodiments, the number of supramacromolecules formed by the rearrangement will be half of the original number of supramacromolecules.

In one or more embodiments, the new configuration may have half as many metal ions and poly-ligand monomers as that of the original configuration. It should be noted that separation differs from typical "dis-assembly" in that the configuration, i.e. polygonal arrangement, of the smaller molecules is different from the original configuration. In these or other embodiments, the number of supramacromolecules formed by the rearrangement will be twice the number of original supramacromolecules.

Thus, the present invention provides a process for precise self-assembly and re-arrangement of a three-dimensional terpyridine-based coordination complex, the process comprising the steps of reacting a plurality of terpyridine-containing ligands with at least one metal ion, wherein the metal is selected from the group consisting of $Fe^{+2}$, $Ru^{+2}$, $Os^{+2}$, $Ir^{+2}$, $Zn^{+2}$, $Sn^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$, and combinations thereof, in a preselected molar ratio, to form a self-assembled three-dimensional terpyridine-based coordination complex having a first configuration; and diluting said coordination complex in a suitable solvent, by a factor of at least about 2, whereupon said coordination complex re-arranges to form at least two smaller, substantially identical, three-dimensional terpyridine-based coordination complexes, each having a second configuration that is different from the first configuration.

In one or more embodiments, the triggering event is dilution/concentration. In these embodiments, the amount of dilution or concentration may be advantageously selected to produce precise, predictable results. In one or more embodiments, the amount of dilution or concentration may be expressed relative to the initial concentration of the supramacromolecule coordination complexes that are formed by combining the poly-ligand monomer with metal ions.

Some re-arrangement has been observed with relatively small changes in concentration. Thus, in one or more embodiments, when the concentration of the solution of supramacromolecules is changed by a factor of about two (2) or more, some re-arrangement will occur and the solution will contain a mixture of two configurations.

Advantageously, with selection of appropriate dilution/concentration, complete re-arrangement is achieved. That is, a monodisperse solution of supramacromolecules having a first configuration becomes a monodisperse solution of supramacromolecules having a second configuration. In one or more embodiments, complete re-arrangement is achieved when the amount of supramacromolecule is changed by a factor of at least about 10, i.e. 1-fold, in other embodiments, by a factor of at least about 15, in other embodiments, by a factor of at least about 100, and in other embodiments, by a factor of at least about 1000.

In other embodiments, the amount of dilution may be expressed based upon the actual concentration of the coordination complex. For example, it has been found that when a solution of a coordination complex is diluted from a concentration of about 12 mg/mL to a concentration of about 0.5 mg/mL or less, the coordination complex undergoes complete re-arrangement.

In one or more embodiments, a change in the configuration of the supramacromolecule may be triggered through the use of light. In these or other embodiments, a supramacromolecule-nanotube network may be prepared from poly-ligand monomers having photoreactive groups. In one or more embodiments, the photoreactive group either forms or breaks one or more bonds when exposed to light, thereby leading to supramacromolecular re-arrangement. In one or more embodiments, light and dilution/concentration may be employed jointly as a triggering event.

As noted above, the supramacromolecules may include additional substituents that are functional groups, molecular groups, or coordination complex groups. The substituents may be present as a result of employing a functionalized or complexed poly-ligand monomer, such as shown in FIGS.

10-12. In other embodiments, the supramacromolecules may be further reacted after self-assembly to incorporate functional groups, molecular groups, or coordination complex groups.

In one or more embodiments, supramacromolecules of the present invention may include repetitively branched, dendritic portions. Thus, embodiments of the supramacromolecules of the present invention may be referred to as dendrimers, or metallodendrimers. In one or more embodiments, the dendrimer may extend from the anchoring group of a poly-ligand monomer. For example, when the poly-ligand monomer includes a bridged anthracene anchoring group, the dendrimer may extend from the anthracene bridge or be coupled via a coupling group to the anthracene bridge. Exemplary dendrimers may be found in U.S. Pat. Nos. 5,863,919, 6,399,717, 7,250,534, 7,368,512, and 8,138,301, and U.S. Pat. Publ. Nos. 2005/0008571, 2010/0133471, and 2010/0041859, all of which are incorporated by reference.

In one or more embodiments, supramacromolecules of the present invention may be used for encapsulation. For the purposes of this specification, the matter to be encapsulated may be referred to as a payload. Suitable payloads include drug active ingredients, proteins, oligomers, polymers, peptides, dyes, salts, solvents, and toxic materials, porphyrins, fullerenes, carbon nanotubes, and extended aromatics.

The payload may be encapsulated and released by multiple methods.

In one or more embodiments, a payload may be encapsulated by supplying a payload in a solvent; and combining poly-ligand monomers and metal ions in the solvent, and allowing poly-ligand monomers and metal ions to self-assemble into a supramacromolecule thereby encapsulating the payload.

In another embodiments, a payload may be encapsulated by supplying a supramacromolecule in a first configuration and a molecule in a solvent; and increasing the concentration of the supramacromolecule in the solvent to effect the self-assembly of the polyhedron into a second configuration thereby encapsulating the payload.

In one or more embodiments, a payload may be released by supplying a supramacromolecule with a molecule encapsulated therein, where the supramacromolecule comprises poly-ligand monomers coordinated to metal ions; and decreasing the concentration of the supramacromolecule thereby releasing the payload. In these or other embodiments, the step of decreasing the concentration of the supramacromolecule causes the poly-ligand monomers and the metal ions to self-assemble into a second supramacromolecule conformation, and the molecule is released during the self-assembly of the second supramacromolecule conformation.

In certain embodiments, the payload may be an active pharmaceutical ingredient. In these or other embodiments, the supramacromolecule may be used to deliver a drug to a patient. In one or more embodiments, an encapsulated pharmaceutical active ingredient may be released by administering a pharmaceutical active ingredient encapsulated in a supramacromolecule to a patient in need thereof, where the supramacromolecule comprises poly-ligand monomers coordinated to metal ions; allowing the supramacromolecule to dilute to a concentration within the patient sufficient to effect a configuration change the supramacromolecule, thereby releasing the pharmaceutical active ingredient. In these or other embodiments, the supramacromolecule may include a targeting moiety suitable for target delivery of the active pharmaceutical ingredient.

In one or more embodiments, the supramacromolecule encapsulates an active pharmaceutical ingredient, the supramacromolecule and the active pharmaceutical ingredient may be included in a pharmaceutical composition. Pharmaceutical compositions may include active pharmaceutical ingredient encapsulated in a supramacromolecule and at least one pharmaceutically acceptable excipient. The pharmaceutical compositions include those suitable for subdermal, inhalation, oral, topical or parenteral use. Examples of pharmaceutical compositions include, but are not limited to, tablets, capsules, powders, granules, lozenges, or liquid preparations.

Tablets and capsules for oral administration may be in unit dose presentation form, and may contain conventional excipients such as binding agents, for example syrup, acacia, gelatin, sorbitol, tragacanth, or polyvinylpyrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulfate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerin, propylene glycol, or ethyl alcohol; preservatives, for example methyl or propyl p-hydroxybenzoate or sorbic acid, and, if desired, conventional flavoring or coloring agents.

As noted above, a supramacromolecule may be use to encapsulate nanotubes. In certain embodiments, the supramacromolecule may partially encapsulate a nanotube. In these or other embodiments, one, or both, ends of the nanotube may span outside of the supramacromolecule. In certain embodiments, one nanotube may be partially encapsulated by multiple supramacromolecules.

In one or more embodiments, a nanotube may be partially encapsulated on both ends by supramacromolecules. In these or other embodiments, system of nanotubes may be assembled connected by supramacromolecules. The system of nanotubes may be referred to as a supramacromolecule-nanotube network. In one or more embodiments, the supramacromolecule-nanotube network may be used to trap a molecule. For example, the ability of the supramacromolecules to change conformations or self-assemble may be used to assemble the supramacromolecule-nanotube network and encapsulate a molecule or payload simultaneously.

For parenteral administration, fluid unit dosage forms are prepared utilizing the compound and a sterile vehicle, water being preferred. The compound, depending on the vehicle and concentration used, can be either suspended or dissolved in the vehicle or other suitable solvent. In preparing solutions, the compound can be dissolved in water for injection and filter sterilized before filling into a suitable vial or ampoule and sealing. Advantageously, agents such as local anesthetics, preservatives and buffering agents etc. can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

The tetrakisterpyridinyl ligand 3 was prepared (67%) using a Suzuki-coupling reaction by treatment of 2,3,6,7-tetrakis(4-bromophenyl)-9,10-dimethyl-9,10-ethanoanthracene (1), which was obtained by the direct bromination ($Br_2$) of the commercially available 9,10-dimethyl-9,10-ethanoanthracene, with 4 equivalents of 4-([2,2':6',2]-terpyridinyl)phenylboronic acid (2). The $^1H$ NMR spectrum of ligand 3 (FIG. 2) exhibited one set of expected signals attributed to the terpyridinyl moieties and a single set of peaks assigned to the newly introduced aryl groups suggesting free rotation throughout the two sets of 60° juxtaposed arms.

The one-step, self-assembly (FIG. 2) of monomer 3 with a precise ratio (1:2) of $Zn(NO_3)_2$ in a stirred mixture of MeOH and $CHCl_3$ (1:1, v/v) at 25° for 1 h was achieved giving a translucent pale yellow solution, which when treated with saturated aqueous $NH_4PF_6$ (to exchange $NO_3^-$ for $PF_6^-$) gave (>98%) the desired 4, as a light yellow precipitate; the structural confirmation was subsequently achieved using 1D and 2D NMR, DOSY NMR, ESI-TWIM-MS, TEM imaging, and single crystal X-ray crystallography. Notably, characterization of the more labile $Cd^{2+}$ analog 5 mirrored that of the $Zn^{2+}$-based sphere 4, with the exception of overlapping of the 4,4''- and 6,6''-tpyHs and the outermost aryl Hs in the $^1H$ (Ha for 3, FIG. 2) and COSY NMR; as well, the MS data are essentially identical.

The $^1H$ NMR spectrum of 4 [FIG. 2, acquired in DMF-$d_7$ and $CD_3CN$ (1:4, v/v)] exhibited a single set of sharp peaks indicating the formation of a single and highly symmetrical species, in which all identically positioned nuclei are chemically and magnetically equivalent. The COSY and NOESY NMR experiments were used to aid and verify the assignments of the $^1H$ NMR spectrum.

The expected upfield shift of the doublet from 8.75 to 7.95 ppm ($\Delta\delta$=0.8 ppm), attributed to the 6,6''-tpyHs, is indicative of the formation of the pseudo-octahedral, bisterpyridine complex and the resultant $H^6$ positioning near the aromatic ring current of the perpendicularly opposed terpyridine. All other signals show the characteristic downfield shifts following complex formation. Notably, the large, rigid complex 4 displays a $^1H$ NMR spectrum that is well-resolved with sharp, easily assignable peaks with only the methyl and bridging methylene protons exhibiting broadening, in contrast to other cage-like pyridine-palladium complexes.

The $^1H$ 2D DOSY NMR spectrum of complex 4 shows a single band with a diffusion coefficient D=$1.99\times10^{-10}$ (log D=−9.69), along with a corresponding solvent band (log D=8.40), indicative of a single species in the DMF-$d_7$ and $CD_3CN$ (1:4, v/v) solution. The calculated diameter of the spherical complex, according to the viscosity of these mixed solvents measured before (0.00422 poise), is 5.18 nm, which is totally consistent with and in agreement with the modeling of the structure, as well as the TEM results.

The ESI-MS (ElectroSpray Ionization-Mass Spectroscopy) spectrum of the 24[<tpy-$Zn^{2+}$-tpy>] 48$PF_6^-$ complex 4 further supports the structure of the cuboctahedron by revealing a series of dominant peaks at m/z 942.3, 989.6, 1041.2, 1097.7, 1159.9, and 1228.6, corresponding to charge states ranging from 24+ to 19+, respectively. These MS results provide strong support for the combination of 12 ligands and 24 $Zn^{2+}$ metal ions along with the experimental m/z values for each charge state and are consistent with the corresponding calculated values. Additional support for 4 was provided by ESI-TWIM-MS experiments [ESI-MS coupled with traveling-wave ion mobility spectrometry (TWIM-MS), a variant of ion mobility spectrometry]. TWIM-MS resembles molecular separation, such as chromatography, separating ions by their charge and shape/size in the TWIM region, followed by m/z in the adjoining mass analyzer. This method provides a tool to resolve isomeric ions and determine structural information that serves as a unique complement to more traditional characterization procedures. The TWIM-MS spectrum exhibits charge states ranging from 24+ to 19+, derived from 4 with a single and narrow band for each charge state and a narrow drift time distribution for the signals extracted for each band, clearly indicating a single species; this is consistent with the NMR results.

The stability of complex 4 was probed with gradient tandem MS (g$MS^2$). The 19+, 11+, and 8+ charge ions (corresponding to the m/z 1228, 2227, and 3116, respectively) were isolated and subjected to collisionally activated dissociation (CAD) with Ar gas prior to ion mobility separation at collision energies ranging from 10 to 100 eV, respectively. The cuboctahedron exhibits good stability, in agreement with other high charge ions of <tpy-$Zn^{2+}$-tpy> complexes. Only when the collision energy reached 37 eV did the 19+ complex ion (m/z 1228) completely disappear, yielding several fragments. Notably, lower charged ions exhibited extreme stability in g$MS^2$ experiments; for example, the 8+ charge ion (m/z 3116) did not completely disappear until the collision energy reached 95 eV. This suggests that the stability of the complex is greater with a higher number of "protective" surrounding anions.

Figure 3:
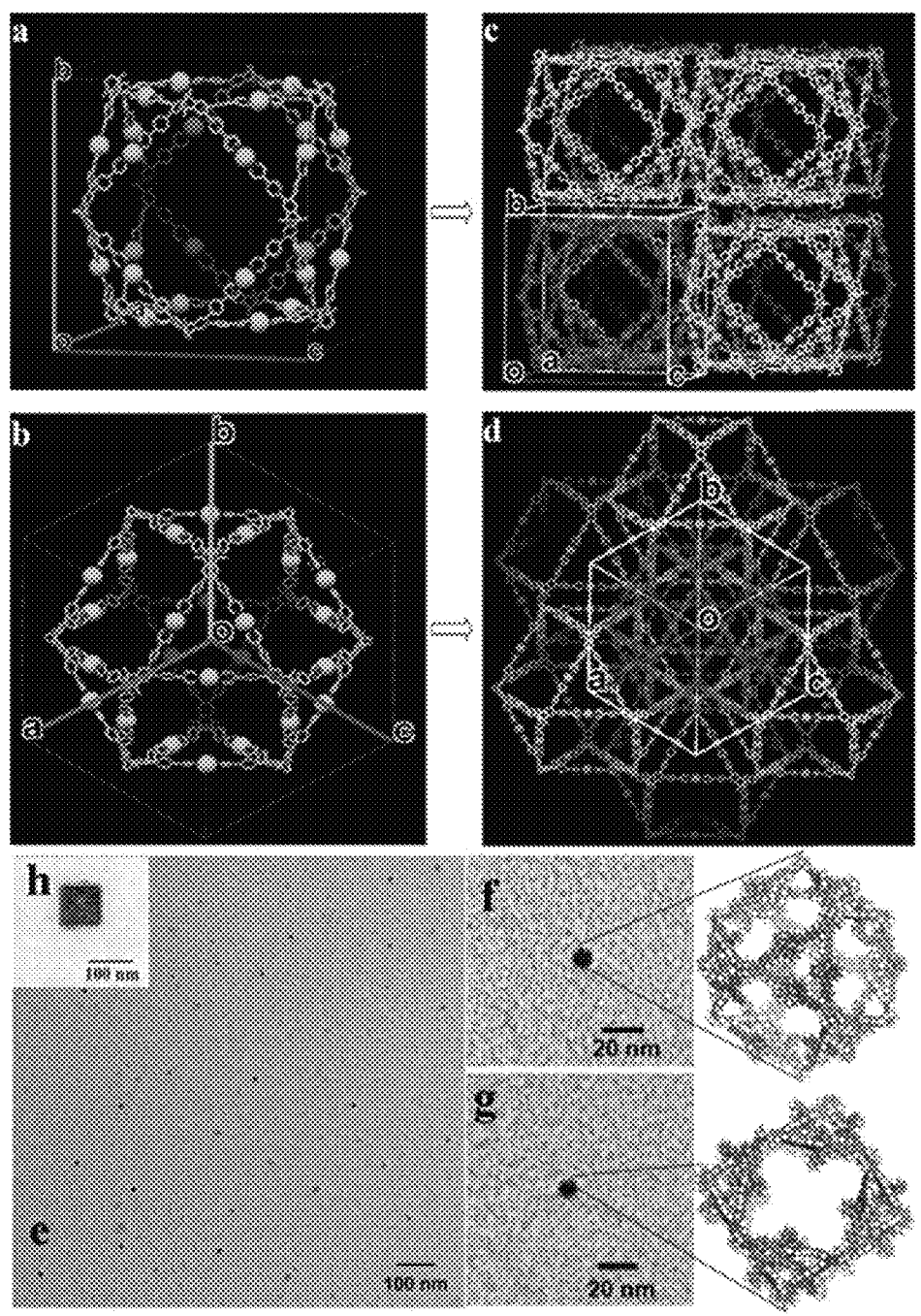
FIG. 3 provides the single crystal structure of complex 4 viewed (3a) from an angle relative to the a, c plane [the (−6.23 1 1.96) direction] and (3b) along the diagonal [the (1 1 1) direction] and as a packing of 8 molecules viewed from the corresponding directions [(3c) and (3d), respectively]. The cuboctahedron molecules pack into cubic crystal in cubic space group. The outer, adjacent pyridinyl rings of each of the 48 terpyridine triads were highly disordered; thus, these groups along with all the hydrogens have not been included in the structural model based on X-ray diffraction. Crystal data: Space group Pm-3m, a=b=c=47.881(1) Å, V=109772(34) Å$^3$, Z=1. Residual R1=0.1827 [I>2σ(I)], and goodness-of-fit=1.039 for $Zn_{24}L_{12}\cdot 48PF_6^-$ ($C_{1224}H_{840}F_{288}N_{144}P_{48}Zn_{24}$, 26092.85 D). And the TEM imaging of complex 4 (bottom image) shows a homogeneous field of similar sized objects (e) while, higher magnification images display the classic cuboctahedron (f) hexagonal and cubic shapes (g). In addition, images were obtained showing the higher order packing potential of 4; the inset image (h) is estimated to contain 19 molecules on a side.

Suitable, colorless, cubic, single crystals for X-ray analysis (FIG. 3) were obtained after two months by vapor diffusion of EtOAc into a DMF:MeCN (1:1, v/v) solution of complex 4. Crystals in the mother liquor were sealed in a quartz capillary and maintained at 25° C. during data collection using synchrotron X-ray radiation. Due to the large volume of the spherical complex (in the size range of small proteins) and the high number of disordered counterions and solvent molecules, the diffraction spots, not unexpectedly, were observed only to an ca. 1.6 Å resolution. It was, however, sufficient to model the positions of the essential core elements of the 12 ligands and the 24 $Zn^{2+}$ ions, thereby leading to the cuboctahedral structure of complex 4, which is consistent with the computer generated model. As expected, a highly symmetric and shape-persistent structure showing the 14 faces with the requisite 24 edges and 12 vertices was revealed supporting the classic cuboctahedron structure with $O_h$ symmetry. The 24 metals form a rhombicuboctahedron conformation with triangles and unequal sided rectangles in which the greatest distance between two $Zn^{2+}$ ions is 4.9 nm, an average distance across the interior is ~40 Å, and the inner void volume is ca 46800 Å$^3$.

Further evidence confirming the cuboctahedron's structure was provided by CCS data (Collision Cross-Section) as determined from the drift times measured in the TWIM-MS experiments. CCS can be viewed as the rotationally averaged, forward moving surface area of the cuboctahedron. For the 15+, 17+, and 20+ charge states of cage 4, the CCSs are 3014.2, 2983.8, and 2888.5 Å$^2$, respectively. The slight CCS differences between these three charge states (balanced by 33, 31, and 28 $PF_6^-$ counterions, respectively) indicate that 4 possesses a rigid and shape-persistent architecture. The average experimental CCS (2931.3 Å$^2$) agrees well with the theoretically predicted CCS for the counterion-free complex (2720 Å$^2$), which was calculated from the corresponding energy minimized structure using the trajectory method that rigorously considers the collision process between ions and buffer gas in the ion mobility region. The differences between the experimental and theoretical CCS are most likely due to the effect of the anions. It was observed in the data that the experimental CCS gradually decreases with increasing charge suggesting the anions contribute less to the CCS at high charge densities.

Transmission electron microscopy (TEM) facilitated visualization of metallomacrocyclic cage 4, directly revealing both the size and shape of individual molecules upon deposition of a dilute MeCN:DMF ($10 0^{-7}$ M, 4:1, v/v) solution of 4 with $PF_6^-$ counterions on carbon-coated grids (Cu, 400 mesh, FIG. 3e). At higher magnification, the images of single molecules, poised on different faces, exhibit the hexagonal and cubic shapes defined by cuboctahedron architecture (FIGS. 3f and 3g). The ability of these polymetallic complexes to pack into aggregates was confirmed with the observation of large, regular, cubic species (FIG. 3h), where in the pictured case, 19 molecules are estimated to be arranged linearly on each edge.

Dilution of $Zn^{2+}$-based cuboctahedron 4 resulted in the observation of a poorly resolved ESI-MS spectrum but still indicated the presence of a new species possessing one-half the molecular weight of 4. Accordingly, diluting the $Cd^{2+}$ cuboctahedron 5, possessing the more labile <tpy-$Cd^{2+}$-tpy> connectivity, using $PF_6^-$ counterions, led to a mixture of 5 and the low molecular weight species 6; further dilution converted the bulk of the material to a octahedral structure 6, possessing 12 $Cd^{2+}$ and 24 $PF_6^-$. ESI-MS was subsequently employed to follow the postulated transformation of sphere 5 from one motif to the smaller sphere 6a. Attempts to isolate and fully characterize this new structure subsequently focused on the use of differing counterions during the self-assembly reactions.

Figure 4:
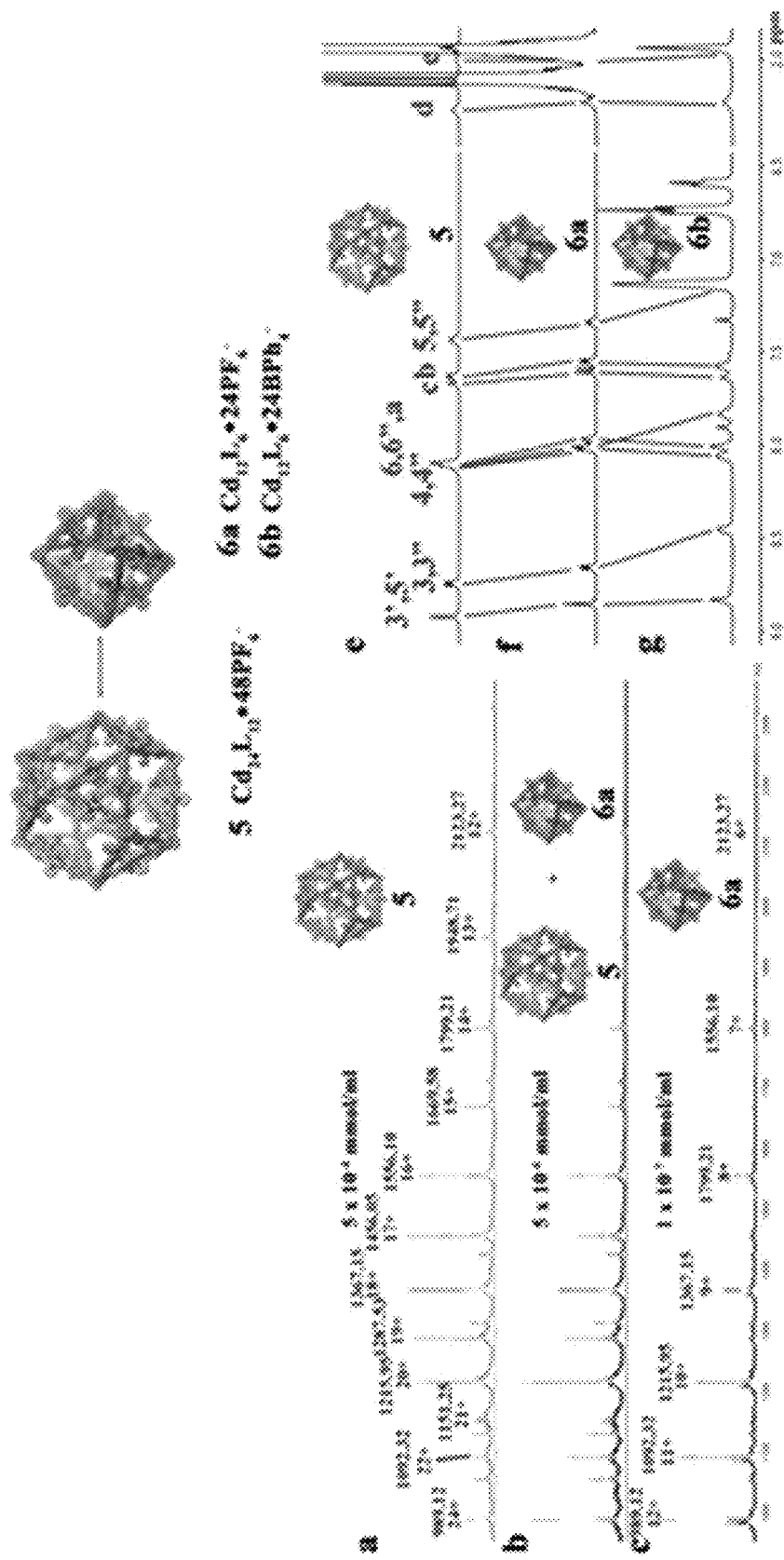
FIG. 4 provides the ESI-MS spectra of the cuboctahedron [(a), $5 \times 10^{-4}$ mmol/mL], the cuboctahedron-octahedron mixture obtained upon dilution of the cuboctahedron [(b), $5 \times 10^{-6}$ mmol/mL] and the octahedron architecture ultimately obtained upon further dilution [(c), $1 \times 10^{-7}$ mmol/mL]. The dynamic equilibrium between cuboctahedron ($Cd_{24}L_{12}$) 5 and octahedron ($Cd_{12}L_6$) 6 and pertinent $^1$H NMR spectra of (e) cuboctahedron-shaped complex 5 with $PF_6^-$, as the anion ($CD_3CN$, $5 \times 10^{-4}$ mmol/L); (f) octahedron-shaped complex 6a with $PF_6^-$, as the anion ($CD_3CN$, 1×10⁻⁴ mmol/L); and (g) octahedron-shaped complex 6b with BPh$_4^-$, as the anion (CD$_3$CN, DMF-d$_7$, 4:1 v/v, 5×10⁻⁴ mmol/L).

Upon switching the counterion from $PF_6^-$ to $BPh_4^-$, the same ligand self-assembled to give (>95%) exclusively the octahedral cage-shaped complex 6b, which was readily proven by NMR spectroscopy (FIGS. 4f and g) and ESI-TWIM-MS. The $^1$H NMR spectrum of complex 6b exhibited a well-resolved set of signals with symmetry (FIG. 4O expected for the octahedron, indicative of a single species possessing a high degree-of-molecular-symmetry; notably, all the $^1$H NMR peaks show upfield shifts, relative to the spectrum arising from the cuboctahedron.

Thus, the cuboctahedron is favored at higher concentrations, and upon dilution a re-arrangement occurs (molecular fission), which gives rise to two equivalents of the octahedron 6. Upon concentration the re-arrangement is reversed (molecular fusion), which regenerates the original cuboctahedron 5. It appears that the number of particles in unit volume decreased correspondingly until entropic force pushed the self-assembled complex to switch into the smaller octahedron structure. It is theorized that entropy plays a critical role in this example of molecular fusion and fission of these very large structural interchanges via either changing the size of counter ions or compound concentration.

In summary, a method is provided for quantitative synthesis of a terpyridine-based, cuboctahedron-shaped supra-macromolecule through a single-step, self-assembly of 12 novel tetradentate terpyridinyl monomer molecules with 24 $Zn^{2+}$ ions. Unequivocal traditional characterization was accomplished along with its single crystal X-ray structure. This nanoscale [24<tpy-$Zn^{2+}$-tpy>][48$PF_6^-$] cuboctahedron (4) with its large cavity shows great potential for drug transport and host-guest chemistry, as suggested by its similarity to known biological complexes, such as the coat protein complex II (COPII) involved in cellular vesicle creation. The novel dynamic structural interconversion of its corresponding $Cd^{2+}$ complex using the same ligand self-assembles into two different structures, which are cuboctahedron-shaped [24<tpy-$Cd^{2+}$-tpy>][48$PF_6^-$] (5) and octahedron-shaped [24<tpy-$Cd^{2+}$-tpy>][48$PF_6^-$] (6). This molecular-level fission or fusion could be easily tuned by simply changing the concentration; the effects of the exchange of different sized counterions can also play an important role the overall structural stability. In addition, this synthetic protocol gives access to the construction of large, multi-component architectures that mimic biological molecules using easily synthesized Archimedean-prescribed monomers, thus adding a new series of nanoscale building blocks to the material sciences.

Figure 5:
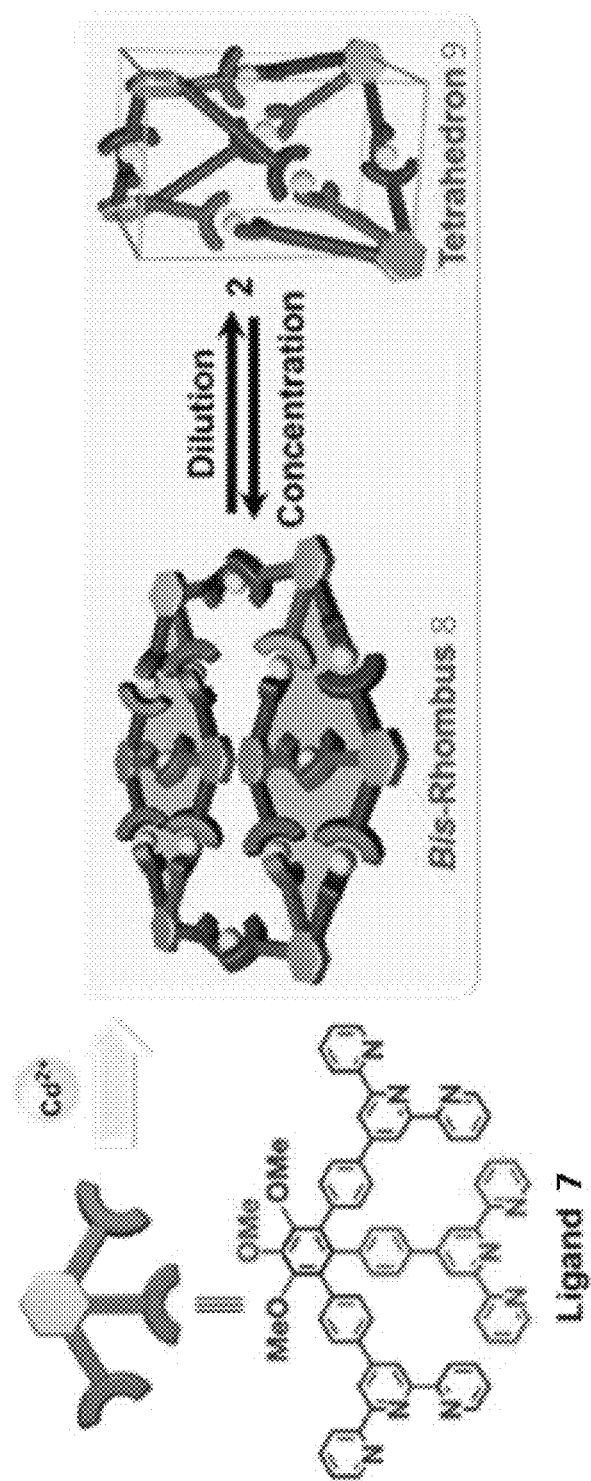
FIG. 5 provides a structure of the tristerpyridine poly-ligand monomer molecule, denoted Ligand 7. The self assembly of tristerpyridine poly-ligand monomer Ligand 7 results in either bis-rhombus 8, and then, upon dilution, tetrahedron 9 is formed.

A terpyridine-based, supramolecular bis-rhombus has been formed by combining ligand 7 and $Zn^{2+}$ ions in the stoichiometric ratio of 2:3. Substitution of $Cd^{2+}$ for $Zn^{2+}$ also formed the architecturally identical bis-rhombus structure 2 (FIG. 5). Preparation was achieved by mixing ligand 7 with $Cd(NO_3)_2 \cdot 4H_2O$ in a precise 2:3 molar ratio in MeOH and stirring at 65° C. for 3 h, followed by cooling to 25° C., and then addition of excess $NH_4PF_6$ to give 8 (>90%); thorough washing with water removed excess inorganic salts. The resultant light-yellow powder was dried in vacuo at 50° C. for 12 h, and characterized directly by ESI-MS and NMR experiments (12 mg-$mL^{-1}$; MeCN or $CD_3CN$, respectively).

The ESI-MS spectrum of complex 8 (FIG. 6A) exhibited a series of peaks with charge states from 6+ to 15+ derived by the successive loss of $PF_6^-$ counterions; based on the mass-to-charge (m/z) ratios of these ions, the molecular weight for 8 is 13550.4 Da, confirming that this complex is composed of precisely eight tristerpyridine ligands (i.e., 1), twelve $Cd^{2+}$ ions, and twenty-four $PF_6^-$ counterions. Isotope patterns for each charge state agreed well with the corresponding simulated isotope patterns, further supporting the complex's constitution. The ESI-TWIM-MS[20] plot further corroborated the mentioned structural assignment (FIG. 6D) by exhibiting a single band with narrow drift time distribution for each charge state, indicating that no other structural conformers, isomers, or other components were present.

The wheel-like complex 8 was also characterized by $^1$H NMR spectroscopy (FIG. 7A), which showed seven different tpy units with the expected integration ratio, albeit with noticeable yet resolvable peak overlap, which is consistent with the assigned bis-rhomboidal structure (FIG. 7A; each tpy unit is represented by a different color and assigned with letters from A to G. While the aromatic region of the $^1$H NMR spectrum was complicated due to substantial overlap of peaks arising from the different tpy moieties, assignment of the peaks was readily achieved based on the analysis of high resolution (750 MHz) 2D COSY and 2D NOESY NMR spectra. Pertinent aspects of these spectra include the observation that all of the 6,6" protons from the tpy units were significantly shifted upfield due to electron shielding effects, as is typical for the inherent pseudo-octahedral connectivity of the <tpy-$Cd^{II}$-tpy> components. Further, in the non-aromatic region, the critical OMe markers of 8 exhibited two singlets at 3.99 and 3.86 ppm that were assigned to $H^{ome-d}$ and $H^{ome-e}$ respectively, with a 2:1 integration ratio, along with two multiplets attributed to the overlapping peaks of the remaining OMe groups. The $^{113}$Cd NMR of 8 (FIG. 7E) exhibited four peaks at 401.61, 401.02, 400.60, and 400.15 ppm with a 1:2:1:2 integration ratio that is also consistent with the assigned structure in which 12 $Cd^{2+}$ ions reside in four different structural environments.

Following the unequivocal MS and NMR structural confirmation of the $Cd^{2+}$-based, bis-rhombus 8, a concentration-dependent phenomenon afforded insight into its possible formation. Upon dilution, 8 was transformed into a smaller novel structure, as recorded in both ESI-MS and NMR studies. Thus, when the concentration was reduced from 12 mg·$mL^{-1}$ to 2 mg·$mL^{-1}$, the ESI-MS spectrum revealed that the relative intensity of odd charge states (7+, 9+, 11+, and 13+) was reduced, while the even charge states (6+, 8+, 10+, 12+, and 14+) increased in relative intensity, as a new pattern of charge distribution appeared (FIG. 6B). A further reduction in concentration to 0.5 mg·$mL^{-1}$ led to a complete disappearance of the original charge states from 8 and the appearance of a completely new series of peaks with charge states from 3+ to 10+ (FIG. 6C). The molecular weight deduced from these peaks for the newly formed structure 3 was 6775.2 Da, which is exactly half of the molecular weight of 8, indicating that 9 is composed of precisely four ligands (7), six $Cd^{2+}$ ions, and twelve $PF_6^-$ anions. Each charge state is due to the loss of a different number of $PF_6^-$ counterions. The isotope patterns further confirmed the molecular weight difference. For the same m/z, the charge states of 9 were always half of those recorded for 8, supporting the observation that 9 possessed a molecular weight of 6775.2 Da. ESI-TWIM-MS (FIG. 6E) clearly confirmed that there were two series of charge states arising from the coexistence of two different structures at 2 mg·$mL^{-1}$ and similar intermediate concentrations. The ESI-TWIM-MS plot for 9 (FIG. 6F) contained single bands with narrow drift time distributions for all charge states observed, confirming that 9 was composed of a single architectural isomer.

Figure 7:
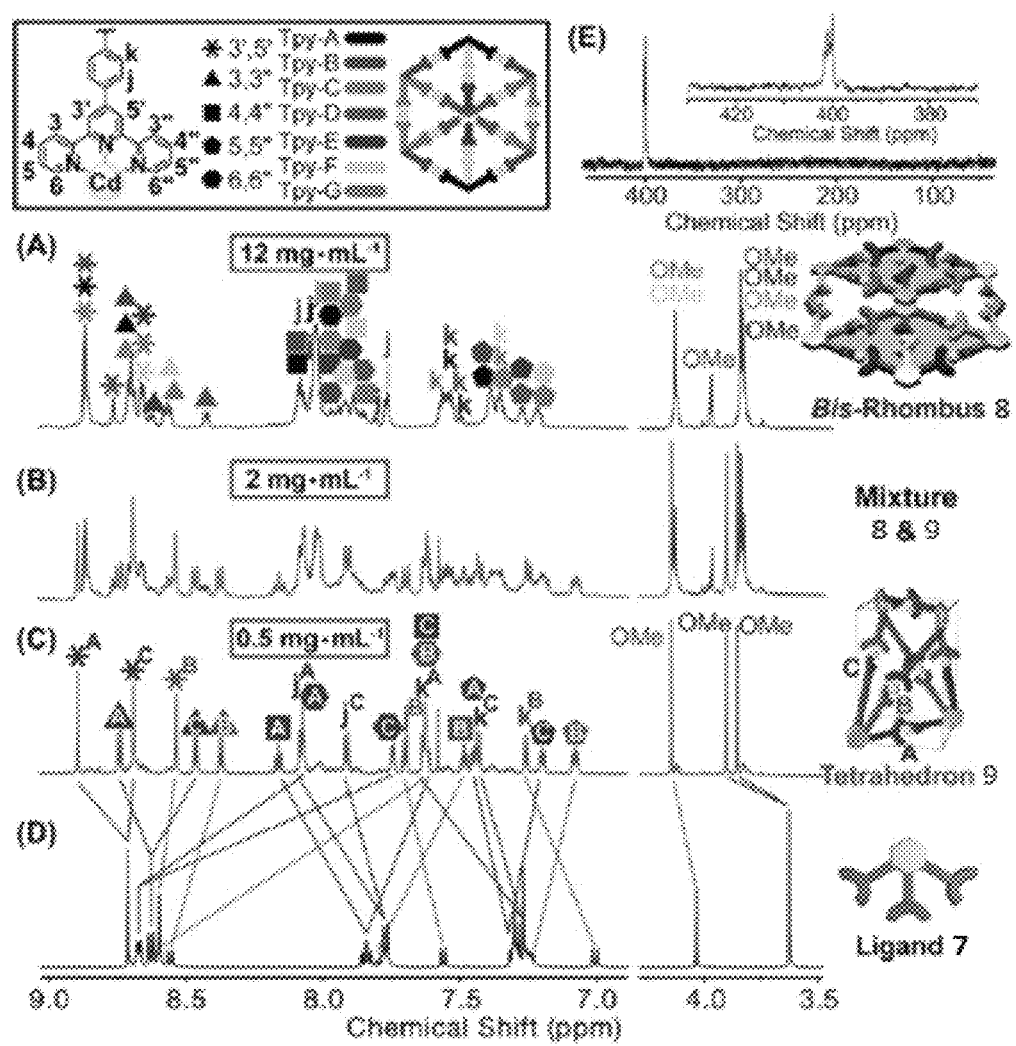
FIG. 7 provides the ¹H NMR spectra (CD$_3$CN, 750 MHz) of (A) bis-rhombus 8 (12 mg·mL⁻¹), (B) mixture of 8 and 9 (2 mg·mL⁻¹), (C) tetrahedron 9 (0.5 mg·mL⁻¹); (D)¹H NMR spectra (CDCl$_3$, 750 MHz) of tristerpyridine poly-ligand monomer Ligand 7, and (E)¹¹³Cd NMR spectra (CD$_3$CN, 110 MHz) for bis-rhombus 2 (20 mg·mL⁻¹). For the bis-rhombus 8 and the tetrahedron 9, different tpy units are denoted by the corresponding letter assignments A through G or A through C, respectively.

The $^1$H NMR also showed the structural changes upon dilution of 8 (FIG. 7). When the concentration was reduced from 12 mg·$mL^{-1}$ to 2 mg·$mL^{-1}$, a new distinct series of peaks (FIG. 7B, red lines) appeared. Upon further dilution, the peaks from 8 (FIG. 7A, blue lines) completely disappeared, leaving only the pristine spectrum for the newly-formed structure 9 (FIG. 7C). The new pattern in the aromatic region showed three different tpy units with equal integration. All of the 6,6" protons from tpy units were shifted upfield supporting the <tpy-$Cd^{+2}$-tpy> connectivity with no evidence of any uncomplexed tpy moieties. The three singlets at 4.16, 3.91, and 3.87 ppm with equivalent integration were assigned to one set of three different $OCH_3$ markers. As in the case of complex 2, all assignments were based on detailed 2D COSY and NOESY.

Figure 8:
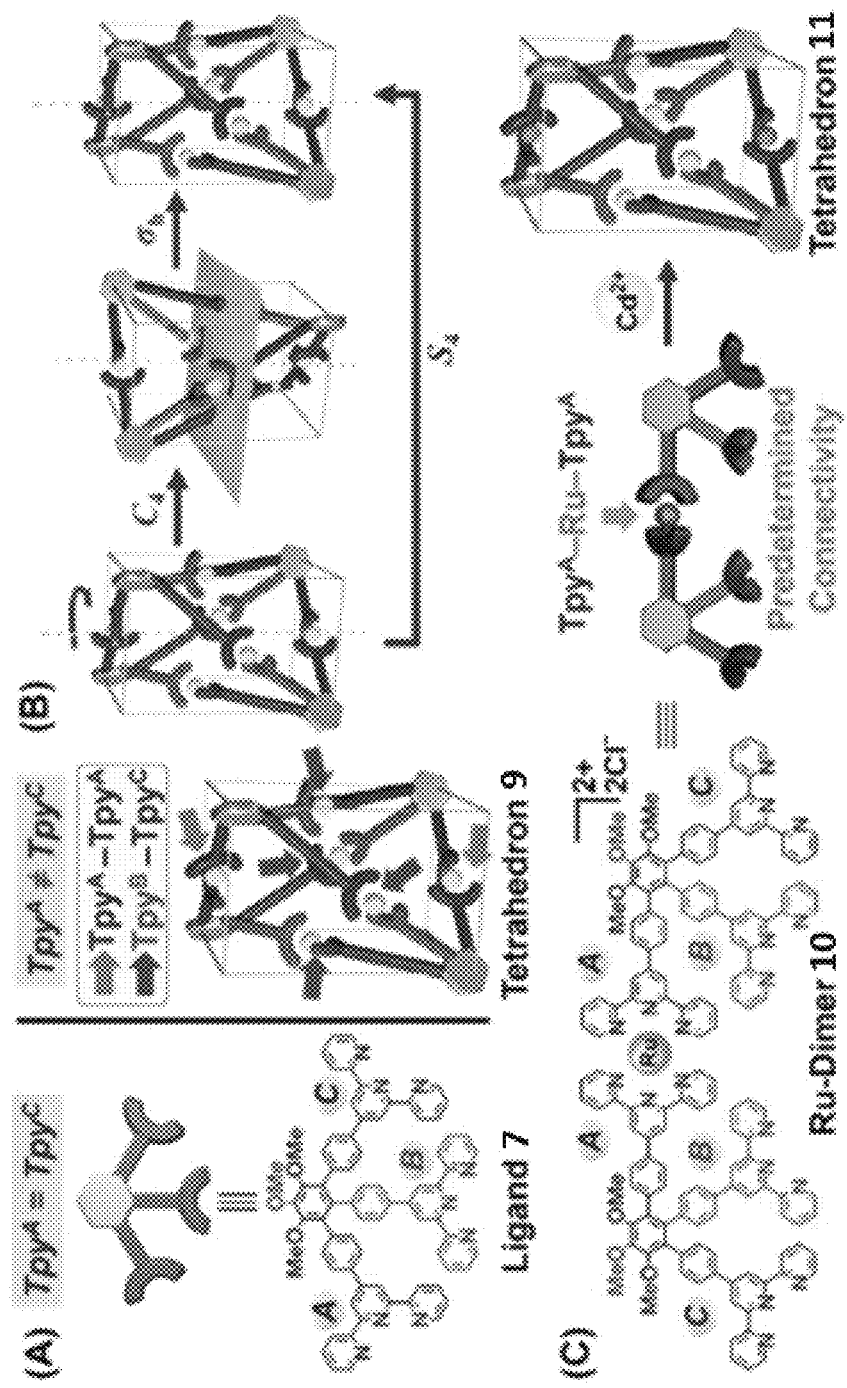
FIG. 8 provides diagrams of (A) Connectivity pattern of complex 9; (B) symmetry operations of S4 symmetry axis in 9; (C) Ru$^{+2}$ dimer 4 with predetermined connectivity and its corresponding tetrahedron 11.
Figure 9:
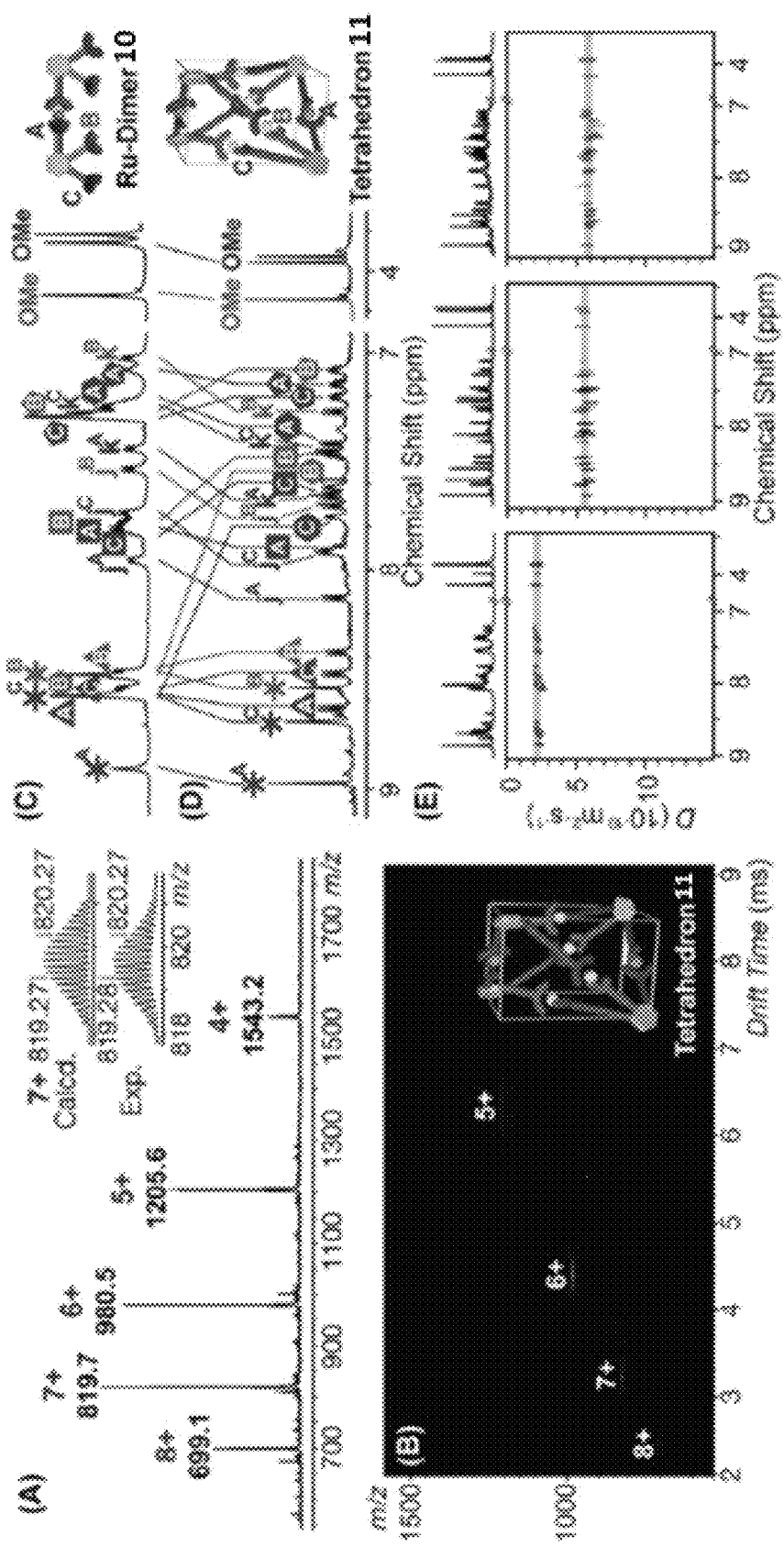
FIG. 9 provides (A) ESI-MS spectrum of 11; (B) 2D ESI-TWIM-MS plot (m/z vs. drift time) for 11. The charge states of intact assemblies are marked; ¹H NMR spectra (CD$_3$CN, 500 MHz) of Ru$^{+2}$-dimer 4 (C) and its corresponding tetrahedron 11 (D); DOSY NMR spectra (CD$_3$CN, 500 MHz) of bis-rhombus 8 (E, left), tetrahedron 9 (E, middle), and tetrahedron 5 (E, right).

These NMR data provide insight into the connectivity of the newly-formed tetrahedral structure 9; all of the terpyridinyl 6,6" proton pairs are shifted upfield indicative of twelve coordinated tpy units (four ligands, each with three tpy) via <tpy-$Cd^{+2}$-tpy> linkages. As well, sharp peaks and a simple NMR pattern indicated a high degree-of-molecular-symmetry, suggesting that the pattern of connectivity is unique and not random. Considering that there are three tpy units ($tpy^A$, $tpy^B$, $tpy^C$, FIG. 8A) in 7, $tpy^A$=$tpy^C$ due to the $C_2$ symmetry; this was confirmed by the distinct 2:1 integration ratio ($^1$H NMR; FIG. 8D) of the two sets of protons from tpy units. Whereas, 9 showed three distinct sets of tpy protons with an 1:1:1 integration ratio; thus, $tpy^A$ and $tpy^C$ are connected, through $Cd^{2+}$, in different ways. In complex 9, the $tpy^C$ from one ligand must always be connected with $tpy^B$ from another ligand, while $tpy^A$ from different ligands are always connected with each other (FIG. 9A). Alternatively, $tpy^B$ must always be connected with $tpy^C$, while $tpy^A$ is only connected to another $tpy^A$. This type of connectivity clearly explains the NMR of the tetrahedron 9 with three different types of tpy units and equivalent integration. The interpretation of the $OCH_3$ markers also permit's insight into the inherent molecular symmetry or asymmetry of the products. Therefore, this newly-formed structure 9 is a quasi-tetrahedron containing a unique $S_4$ symmetry axis (FIG. 8B) and possesses three sets of tpy units giving rise to three different singlets from three different juxtaposed methoxy groups per each hexasubstituted apical phenyl moiety.

To further confirm the connectivity pattern within 9, $Ru^{+2}$-dimer 10 (FIG. 8C) was synthesized in 6 standard steps from commercially available trimethoxybenzene via known methodology which resulted in two $tpy^A$ units from two tristerpyridine ligands 7 being connected via stable <tpy-$Ru^{II}$-tpy> connectivity. When 10 self-assembled with $Cd^{2+}$ ions in MeOH under identical conditions, the connectivity pattern of $tpy^A$ is uniquely predetermined. Thus, if the ligand connectivity pattern based on NMR and MS data (shown in FIG. 8A) was correct for 9, use of dimer 10 would give rise to a similar tetrahedron cage 5 with a nearly identical spectral-derived connectivity pattern. Accordingly, the ESI-MS spectrum of cage 11 (FIG. 9A) exhibited a series of peaks with charge states from 4+ to 8+ derived by the loss of an increasing number of $PF_6^-$ units. From these ions, the molecular weight of 11 was determined to be 6752.7 Da, supporting its composition of precisely two building blocks of dimer 10 (each containing one $Ru^{2+}$), four $Cd^{2+}$ ions, and twelve $PF_6^-$ anions. Isotope patterns of each charge state agreed well with the corresponding simulated isotope patterns. The ESI-TWIM-MS plot (FIG. 9B) further confirmed the structural composition exhibiting charge states with narrow drift time distributions indicating that no other structural conformers or isomers were present. Notably, $^1$H NMR analysis of tetrahedron 11 (FIG. 9D) also revealed three sets of tpy units with equal integration and upfield shifted 6,6" protons for all the tpy units, thereby supporting the presence of <tpy-M"-tpy> (M=Cd or Ru) and no uncomplexed tpy moieties. Assignments were based on detailed analyses of the 2D COSY and NOESY spectra.

In diffusion-ordered NMR spectroscopy (DOSY, FIG. 9E), all of the signals exhibited a narrow band near diffusion coefficients of $2.6 \times 10^{-10}$, $5.5 \times 10^{-10}$, and $5.6 \times 10^{-10}$ $m^2$ $s^{-1}$ for bis-rhombus 8, tetrahedron 9, and tetrahedron 10, respectively, affirming that the size of the tetrahedron is appreciably smaller compared to bis-rhombus 8. The sizes of tetrahedra 9 and 11 are very similar, consistent with the common connectivity type in both these structures.

Collision cross sections (CCSs) were also derived for several of the ions observed in the TWIM-MS experiments (Table 1). The CCS of an ion is a physical property and represents a measure of the corresponding ion size and architecture. The CCSs for all charge states of tetrahedron 9 (864.3±38.8 Å²) were found to be significantly lower than the CCSs for the charge states of bis-rhombus 8 (1578.4±22.5 Å²), which is fully consistent with the respective structures. The CCSs for tetrahedrons 9 and 11 are very similar (864.3±38.8 and 859.5±39.5 Å², respectively), indicating that these constructs possess similar structures with the same connectivity. Theoretical CCSs were also calculated based on 300 candidate structures for each complex (from molecular dynamics simulations), using trajectory (TJ) and exact hard sphere scattering (EHSS) methods. The TJ model provides a more realistic CCS prediction, especially for larger ions, as it considers both long-range interactions and momentum transfer between the ions and the gas in the ion mobility region. The time required to perform TJ calculations is, however, long; in such cases, the EHSS method, which ignores long-range interactions, has been frequently employed. Here, both methods were utilized. For the larger bis-rhombus 8, the average CCS of the 300 simulated structures obtained by the TJ method (1667.7±48.0 Å²) agrees reasonably well with the experimentally deduced average CCS. Conversely, for the smaller tetrahedral complexes 9 and 11, both the EHSS as well as the TJ method predict CCSs that lie within the range of the measured values. It is noteworthy that the CCS calculated for bis-rhombus 8 is approximately twice as large as the CCSs of either tetrahedral complex (9 or 11), in agreement with the presence of twice as many ligands and metal ions in the former.

Finally, gradient tandem MS (gMS²) experiment was performed on charge state 7+ of the assemblies 8 and 9 to examine the intrinsic stability of these complexes. The maximum kinetic energies at which 8 and 9 with 7+ charges survived intact after collisional activation with Ar targets were 57 eV and 27 eV, respectively. The corresponding center-of-mass collision energies, which represent approximate measures of the intrinsic stabilities of the complexes, are 1.27 eV and 1.30 eV, respectively. Thus, there is no significant stability difference between these complexes, strongly suggesting that there is no enthalpically driven preference to form a certain complex and that entropic reasons dictate why 8 and 9 co-exist within a specific or limited concentration range.

A 3D supramolecular quasi-tetrahedron 9 was successfully synthesized in near quantitative yield and its structure was shown to be an elongated quasi-tetrahedron with a single $S_4$ symmetry axis, based on the NMR and MS analysis. Interestingly, the formation of 3 was concentration-dependent and this complex could only be detected at solution concentrations below 12 mg·mL$^{-1}$ and became the only observed assembly below 0.5 mg·mL$^{-1}$. Concentrating a dilute solution, in order to isolate product 9, shifted the structural equilibrium to the bis-rhombus 8, meaning that the $S_4$ quasi-tetrahedron exists under these conditions only at low concentration. Alternatively, 9 may become an unstable intermediate that fragments to generate a specie with one or more broken <tpy-Cd-tpy> connections, which then dimerize to regenerate the more stable, isolated bis-rhombus 8 at higher concentrations. It would thus appear that in the world of 3D supramolecular assembly different unobserved chemical pathways are possible under high dilution conditions. It is worth noting that concentration-dependent aggregation is observed for proteins. The present invention shows that such a phenomenon is also possible with abiotic macromolecules.

TABLE 1

Experimental and theoretical collision cross sections (CCSs) of 8, 9 and 11.

| Charge State | Drift Time (ms) | Exp. | Exp. Avg | Calc. Avg |
|---|---|---|---|---|
| Bis = Rhombus 2 | | | | |
| 9+ | 5.69 | 1552.0 | | 1711.4 ± 41.9 |
| 10+ | 4.78 | 1567.9 | | (EHSS$^a$) |
| 11+ | 4.15 | 1592.5 | | 1667.7 ± 48.0 |
| 12+ | 3.61 | 1601.2 | 1578.4 ± 22.5 | (TJ $^b$) |
| Tetrahedron 3 | | | | |
| 5+ | 6.05 | 892.6 | | 826.6 ± 10.7 |
| 6+ | 4.33 | 891.7 | | (EHSS$^a$) |
| 7+ | 3.16 | 962.8 | | 808.5 ± 14.4 |
| 8+ | 2.36 | 809.9 | 864.3 ± 38.8 | (TJ $^b$) |
| Tetrahedron 5 | | | | |
| 5+ | 6.14 | 899.7 | | 826.6 ± 10.7 |
| 6+ | 4.24 | 881.0 | | (EHSS$^a$) |
| 7+ | 3.07 | 847.3 | | 807.8 ± 15.3 |
| 8+ | 2.35 | 810.0 | 859.5 ± 39.5 | (TJ b) |

$^a$EHHS (exact hard sphere scattering) method;
$^b$ TJ (trajectory) method (both available in the MOBCAL program Provided herein are:

A process for precise self-assembly and re-arrangement of a three-dimensional terpyridine-based coordination complex, the process comprising the steps of:

reacting a plurality of terpyridine-containing poly-ligand monomer molecules with at least one metal ion, wherein the metal is selected from the group consisting of $Fe^{+2}$, $Ru^{+2}$, $Os^{+2}$, $Ir^{+2}$, $Zn^{+2}$, $Sn^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$, and combinations thereof, in a pre-selected molar ratio, to form a self-assembled three-dimensional terpyridine-based coordination complex having a first configuration; and diluting said coordination complex in a suitable solvent, by a factor of at least about 10, whereupon said coordination complex quantitatively re-arranges to form at least two smaller, substantially identical, three-dimensional terpyridine-based coordination complexes, each having a second configuration that is different from the first configuration.

A process for precise self-assembly and re-arrangement of a three-dimensional terpyridine-based coordination complex, the process comprising the steps of:

reacting a plurality of bridged anthracene tetrakis(terpyridine) molecules with at least one metal ion, wherein the metal is selected from the group consisting of $Fe^{+2}$, $Ru^{+2}$, $OS^{+2}$, $Ir^{+2}$, $Zn^{+2}$, $Cu^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$, and combinations thereof, in a pre-selected molar ratio, to form a self-assembled three-dimensional terpyridine-based coordination complex having a first configuration; and diluting said coordination complex in a suitable solvent, by a factor of at least 10, whereupon said coordination complex quantitatively re-arranges to form at least two smaller, substantially identical, three-dimensional terpyridine-based coordination complexes, each having a second configuration that is different from the first configuration.

A cuboctahedral terpyridine-based supramacromolecule comprising a plurality of bridged anthracene tetrakis (terpyridine) molecules complexed to a plurality of metal ions, and wherein the diameter of the supramacromolecule is at least about 4 nanometers, in other embodiments, at least about 5 nanometers, in other embodiments, at least about 6 nanometers.

A cuboctahedral terpyridine-based supramacromolecule that is formed by combining a plurality of bridged anthracene tetrakis(terpyridine) molecules with a plurality of metal ions selected from the group consisting of $Fe^{+2}$, $Ru^{+2}$, $Os^{+2}$, $Ir^{+2}$, $Zn^{+2}$, $Sn^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$, and combinations thereof, in a molar ratio of about 1:2.

A metallodendrimer that is formed by a process comprising the step of combining a plurality of bridged anthracene tetrakis(terpyridine) molecules with a plurality of metal ions selected from the group consisting of $Fe^{+2}$, $Ru^{+2}$, $Os^{+2}$, $Ir^{+2}$, $Zn^{+2}$, $Cn^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$, and combinations thereof, in a molar ratio of about 1:2.

A supramolecular capsule that is formed by combining a plurality of bridged anthracene tetrakis(terpyridine) molecules with a plurality of metal ions selected from the group consisting of $Fe^{+2}$, $Ru^{+2}$, $Os^{+2}$, $Ir^{+2}$, $Zn^{+2}$, $Sn^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$, and combinations thereof, in a molar ratio of about 1:2.

A method of releasably encapsulating a payload in a supramolecular capsule, the method comprising the steps of:
providing a solution comprising a payload, a carrier, and a first three-dimensional terpyridine-based coordination complex having a first configuration, wherein the complex is formed by reacting a plurality of terpyridine-containing poly-ligand monomer molecules with at least one metal ion, wherein the metal is selected from the group consisting of $Fe^{+2}$, $Ru^{+2}$, $Os^{+2}$, $Ir^{+2}$, $Zn^{+2}$, $Sn^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$, and combinations thereof, in a pre-selected molar ratio, wherein the coordination complex is present in an amount of from about $1 \times 10^{-4}$ to about 12 mmol/mL;
diluting said solution by a factor of at least about 10 with a solvent, wherein said step of diluting causes said coordination complex to quantitatively re-assemble into multiple coordination complexes that are smaller relative to said first coordination complex, and that have a second configuration, each smaller coordination complex effectively encapsulating said payload; and optionally, concentrating said solution by a factor of at least 10, wherein said step of concentrating said solution results in the quantitative re-arrangement of said multiple smaller coordination complexes into said first coordination complex, thereby releasing said payload into said solution.

A process for precise self-assembly and re-arrangement of a three-dimensional terpyridine-based coordination complex, the process comprising the steps of:
reacting a plurality of tristerpyridine-based monomer molecules with at least one metal ion, wherein the metal is selected from the group consisting of $Fe^{+2}$, $Ru^{+2}$, $Os^{+2}$, $Ir^{+2}$, $Zn^{+2}$, $Sn^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$, and combinations thereof, in a molar ratio of about 2:3, to form a self-assembled three-dimensional terpyridine-based coordination complex having a first configuration; and diluting said coordination complex in a suitable solvent, by a factor of at least 10, whereupon said coordination complex quantitatively re-arranges to form at least two smaller, substantially identical, three-dimensional terpyridine-based coordination complexes, each having a second configuration that is different from the first configuration.

A tetrahedral terpyridine-based supramacromolecule that may be represented by structure 9 in FIG. 5.

A method for preparing a tetrahedral terpyridine-based metallomacrocycle, the method comprising the steps of:
reacting a plurality of tristerpyridine ligands with at least one metal ion, wherein the metal is selected from the group consisting of $Fe^{+2}$, $Ru^{+2}$, $Os^{+2}$, $Ir^{+2}$, $Zn^{+2}$, $Sn^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$, and combinations thereof, in a molar ratio of about 2:3, to form a self-assembled three-dimensional terpyridine-based coordination complex having a first configuration; and diluting said coordination complex in a suitable solvent, by a factor of at least 10, whereupon said coordination complex quantitatively dis-assembles to form at least two smaller, substantially identical, three-dimensional terpyridine-based coordination complexes, each having a second configuration that is different from the first configuration.

Advantageously, the present invention provides methods for quantitative synthesis of a terpyridine-based, cuboctandron-shaped supramacromolecule through a single-step, self-assembly of twelve novel tetradentate terpyridinyl molecules and 24 metal ions. Embodiments of the present invention provide a shape-persistent, Archimedean-based tetrakis terpyridinyl molecule that self-assembles using cadmium or zinc as the metal, into a large molecular sphere (a cuboctahedron). Upon exposure to a triggering event such as dilution, the cuboctahedron undergoes transformation into two identical octahedral spheres, each possessing precisely one-half the molecular weight of the parent struction. Upon concentration, the octahedral spheres reconstitute solely as the original cuboctahedron, reminiscent of biological fission and fusion processes. This molecular fission or fusion may be easily tuned by simply controlling the concentration. In one or more embodiments, the effects of the exchange of different counter ions may also play an important role in the overall structural stability.

Various modifications and alterations that do not depart from the scope and spirit of this invention will become apparent to those skilled in the art. This invention is not to be duly limited to the illustrative embodiments set forth herein.

What is claimed is:

1. A process for precise self-assembly and re-arrangement of a three-dimensional terpyridine-based coordination complex, the process comprising the steps of:
reacting a plurality of terpyridine-containing poly-ligand monomer molecules with at least one metal ion, wherein the metal is selected from the group consisting of $Fe^{+2}$, $Ru^{+2}$, $Os^{+2}$, $Ir^{+2}$, $Zn^{+2}$, $Sn^{+2}$, $Cu^{+2}$, $Ni^{+2}$, $Ba^{+2}$, $Mg^{+2}$, $Mn^{+2}$, $Cu^{+2}$, $Pb^{+2}$, $Ca^{+2}$, $Cd^{+2}$, and combinations thereof, to form a self-assembled three-dimensional terpyridine-based first coordination complex having a first configuration; and
exposing said first coordination complex to a triggering event selected from the group consisting of change in temperature, change in pressure, change in concentration, exposure to radiation, and combinations thereof, whereupon said first coordination complex re-arranges to form at least two smaller, substantially identical, three-dimensional terpyridine-based coordination complexes, each having a second configuration that is different from the first configuration.

2. The process of claim 1, wherein the terpyridine-containing poly-ligand monomer molecules are bridged anthracene tetrakis(terpyridine) molecules.

3. The process of claim 2, wherein the step of reacting includes the step of selecting a molar ratio of monomer molecules to metal ions, and wherein the selected molar ratio of monomer molecules to metal ions is about 1:2.

4. The process of claim 3, wherein the first configuration is cuboctahedral.

5. The process of claim 4, wherein the step of exposing said first coordination complex to a triggering event comprises the step of diluting said first coordination complex in a suitable solvent, by a factor of at least about 10.

6. The process of claim 5, wherein the second configuration is octahedral.

7. The process of claim 1, wherein the terpyridine-containing poly-ligand monomer molecules are tristerpyridine-based monomer molecules.

8. The process of claim 7, wherein the step of reacting includes the step of selecting a molar ratio of monomer molecules to metal ions, and wherein the molar ratio is 2:3.

9. The process of claim 8, wherein the first configuration is bis-rhombus.

10. The process of claim 9, wherein the step of exposing said first coordination complex to a triggering event comprises the step of diluting said first coordination complex in a suitable solvent, by a factor of at least about 10.

11. The process of claim 10, wherein the step of exposing said first coordination complex to a triggering event comprises the step of diluting said first coordination complex in a suitable solvent, by a factor of at least about 100.

12. The process of claim 11, wherein the second configuration is tetrahedral.

13. The process of claim 1, further comprising the step of exposing at least two of the smaller, three-dimensional terpyridine-based coordination complexes having the second configuration to a triggering event selected from the group consisting of change in temperature, change in pressure, change in concentration, exposure to radiation, and combinations thereof, whereupon said second coordination complexes re-arrange and combine to reform the first coordination complex having the first configuration, thereby reversing said first re-arrangement.

* * * * *